US010280337B2

(12) United States Patent
Niimi et al.

(10) Patent No.: US 10,280,337 B2
(45) Date of Patent: May 7, 2019

(54) METHOD FOR RECYCLING OPTICAL DEVICE CONSTITUENT MEMBERS AND METHOD FOR EVALUATING REWORKABILITY OF OPTICAL DEVICE CONSTITUENT LAMINATE

(71) Applicant: Mitsubishi Chemical Corporation, Tokyo (JP)

(72) Inventors: Kahoru Niimi, Nagahama (JP); Makoto Inenaga, Nagahama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 141 days.

(21) Appl. No.: 15/322,897

(22) PCT Filed: Jun. 30, 2015

(86) PCT No.: PCT/JP2015/068799
§ 371 (c)(1),
(2) Date: Dec. 29, 2016

(87) PCT Pub. No.: WO2016/002763
PCT Pub. Date: Jan. 7, 2016

(65) Prior Publication Data
US 2017/0152404 A1    Jun. 1, 2017

(30) Foreign Application Priority Data

Jul. 1, 2014  (JP) ................................ 2014-136087

(51) Int. Cl.
| | |
|---|---|
| C09J 5/06 | (2006.01) |
| C09J 5/00 | (2006.01) |
| C09J 133/00 | (2006.01) |
| C09J 201/00 | (2006.01) |
| G02B 1/14 | (2015.01) |
| C09J 151/00 | (2006.01) |
| G01N 3/08 | (2006.01) |
| G02B 5/30 | (2006.01) |
| C09J 4/06 | (2006.01) |
| C09J 133/06 | (2006.01) |
| C08F 285/00 | (2006.01) |
| C08F 290/04 | (2006.01) |

(52) U.S. Cl.
CPC . *C09J 5/06* (2013.01); *C09J 4/06* (2013.01); *C09J 5/00* (2013.01); *C09J 133/00* (2013.01); *C09J 133/06* (2013.01); *C09J 151/003* (2013.01); *C09J 201/00* (2013.01); *G01N 3/08* (2013.01); *G02B 1/14* (2015.01); *G02B 5/3033* (2013.01); *C08F 285/00* (2013.01); *C08F 290/046* (2013.01); *C09J 2205/302* (2013.01); *C09J 2451/00* (2013.01); *G01N 2203/0003* (2013.01); *G01N 2203/0017* (2013.01); *G01N 2203/0091* (2013.01); *Y02P 20/582* (2015.11)

(58) Field of Classification Search
CPC ..................................... C09J 5/06; G01N 3/08
See application file for complete search history.

(56) References Cited

U.S. PATENT DOCUMENTS

| | | | |
|---|---|---|---|
| 2003/0121601 A1 | 7/2003 | Tajima | |
| 2010/0210166 A1 | 8/2010 | Toyoda et al. | |
| 2012/0263956 A1 | 10/2012 | Watanabe et al. | |
| 2015/0024651 A1 | 1/2015 | Cho et al. | |
| 2015/0309341 A1 | 10/2015 | Zhang et al. | |

FOREIGN PATENT DOCUMENTS

| | | | |
|---|---|---|---|
| CN | 103950269 A | | 7/2014 |
| JP | 11 095210 | * | 4/1999 |
| JP | 2003-288028 A | | 10/2003 |
| JP | 2004-184677 A | | 7/2004 |
| JP | 2004-231723 A | | 8/2004 |
| JP | 2009-186961 A | | 8/2009 |
| JP | 4971529 B2 | | 7/2012 |
| JP | 2013-3299 A | | 1/2013 |
| JP | 2013-98366 A | | 5/2013 |
| JP | 5203964 B2 | | 6/2013 |
| JP | 2013-181088 A | | 9/2013 |
| WO | 2010/137523 A1 | | 12/2010 |

(Continued)

OTHER PUBLICATIONS

JP 11 095210 machine translation (1999).*

(Continued)

*Primary Examiner* — Kuo Liang Peng
(74) *Attorney, Agent, or Firm* — Oblon, McClelland, Maier & Neustadt, L.L.P.

(57) ABSTRACT

A method for recycling optical device constituent members, wherein a transparent adhesive material is softened by heating and is crosslinked by light irradiation, an optical device constituent laminate having a constitution in which two optical device constituent members are bonded via a transparent adhesive material in a pre-crosslinked state is used as a recycle starting material, and the method including: heating at least the transparent adhesive material of the optical device constituent laminate; standing the optical device constituent laminate; hanging a linear member along an end edge of the transparent adhesive material located at an upper end edge of the optical device constituent laminate; dividing the transparent adhesive material by applying a load by the linear member; and producing the two optical device constituent members to which a divided one-side transparent adhesive material adheres.

11 Claims, 8 Drawing Sheets

(56) References Cited

FOREIGN PATENT DOCUMENTS

| | | |
|---|---|---|
| WO | 2011/045862 A1 | 4/2011 |
| WO | 2014/046182 A1 | 3/2014 |
| WO | 2014/054632 A1 | 4/2014 |

OTHER PUBLICATIONS

JIS-Z-0237 (date unknown).*
Office Action dated Oct. 10, 2017 in Japanese Patent Application No. 2016-531387 (with English language translation).
International Search Report dated Sep. 1, 2015 in PCT/JP2015/068799 filed Jun. 30, 2015.

* cited by examiner

[FIG.1]
(A)
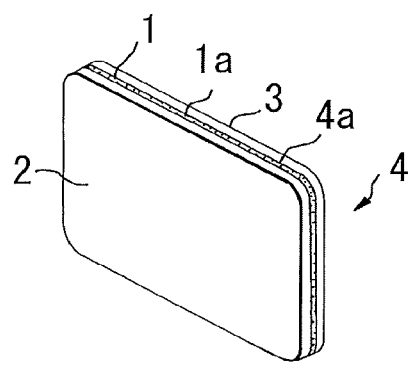
(B)
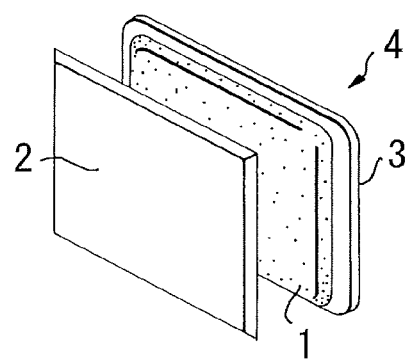
(C)
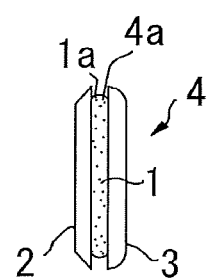

[FIG.2]
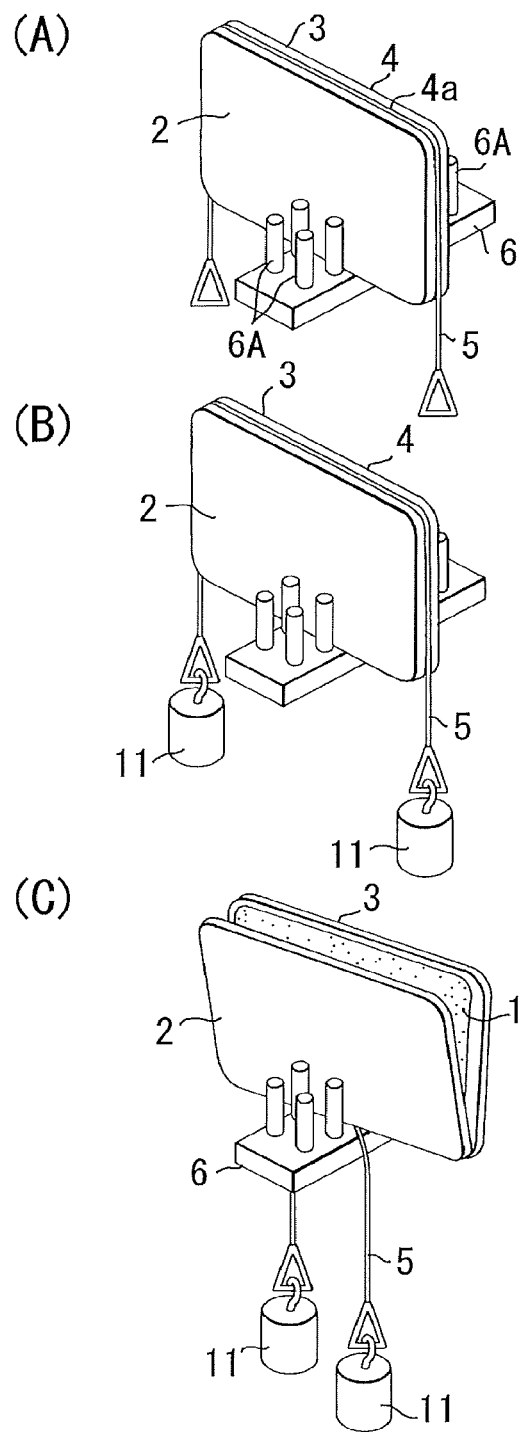

[FIG.3]
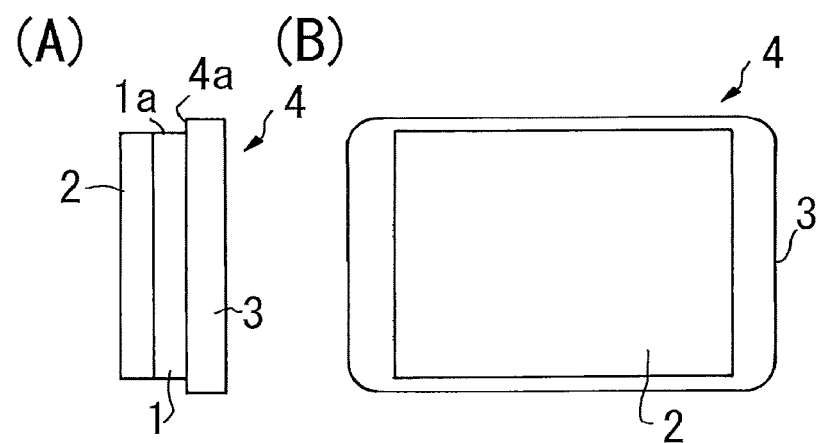
[FIG.4]
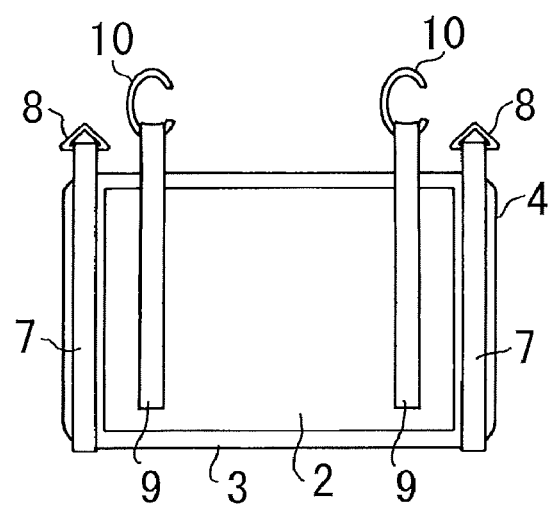

[FIG.5]
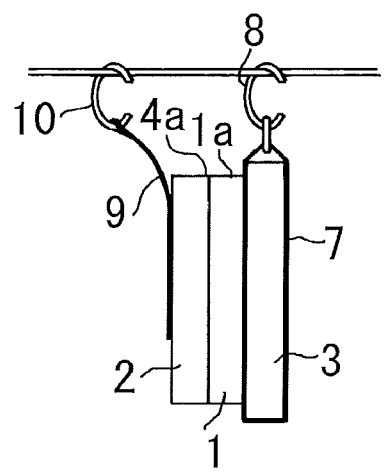
[FIG.6]
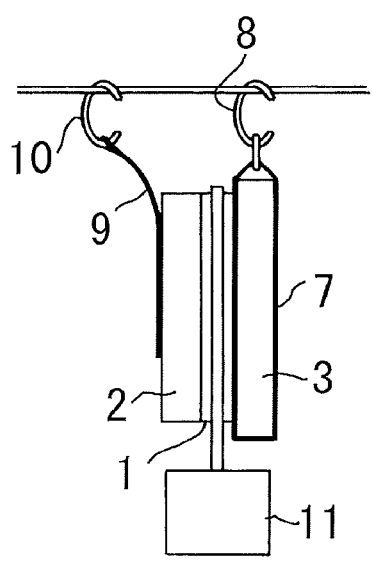

[FIG. 7]
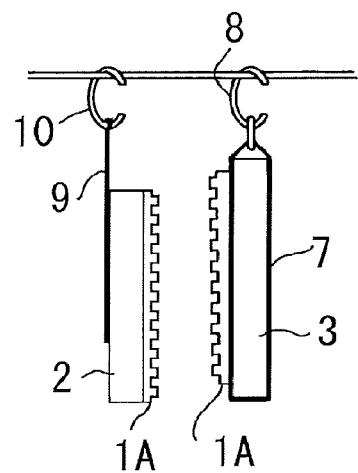
[FIG. 8]
(A)　　　　　　　　　　(B)
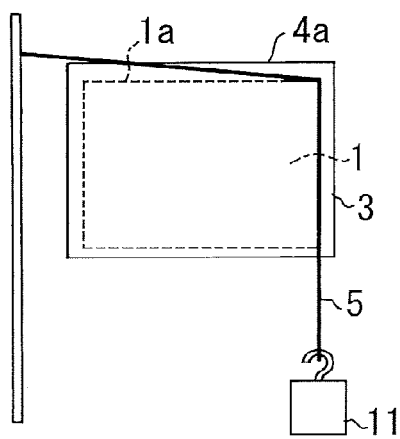 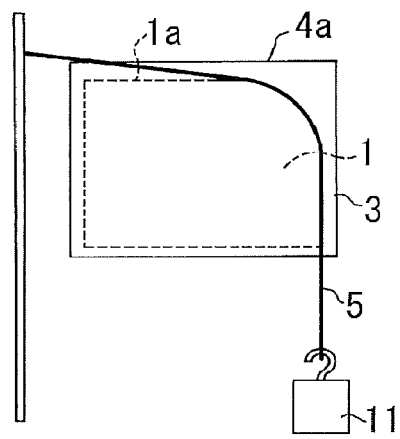

[FIG. 9]
(A)
(B)
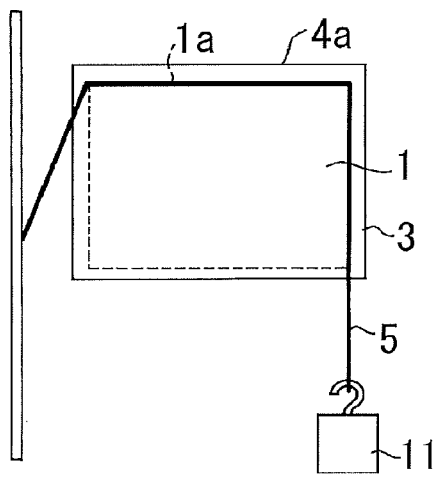
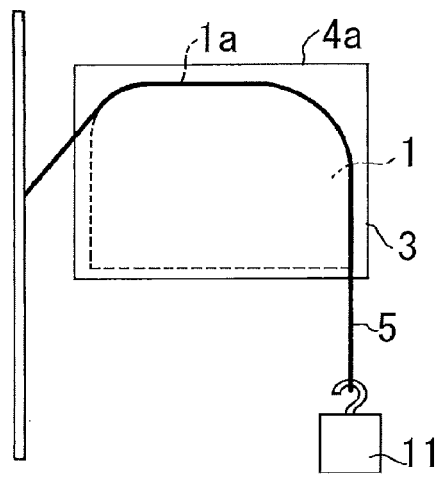

[FIG.10]
(A)
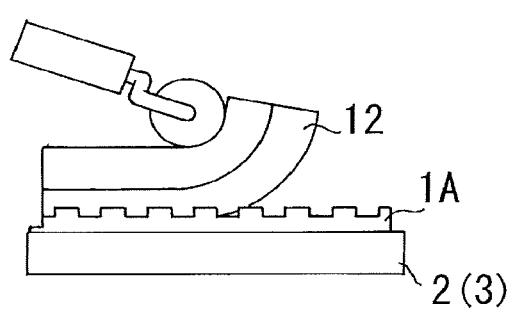
(B)
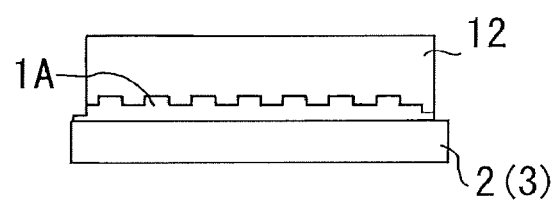
(C)
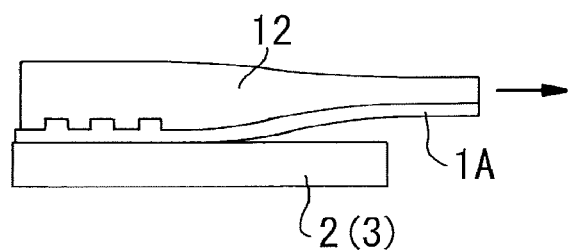

[FIG. 11]
(A)
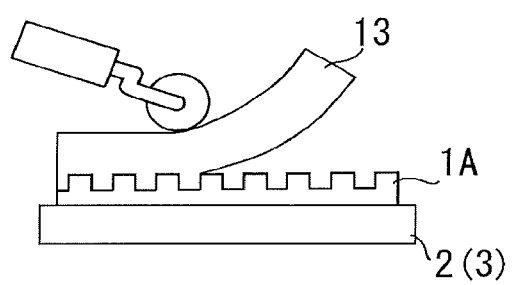
(B)
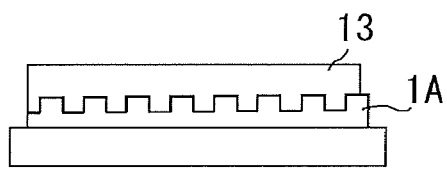
(C)
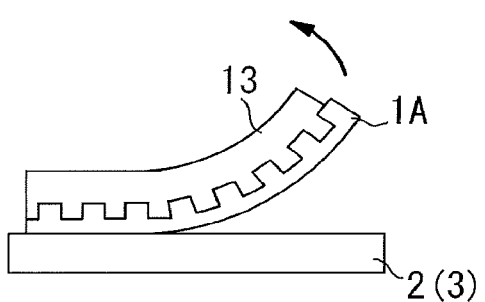

METHOD FOR RECYCLING OPTICAL DEVICE CONSTITUENT MEMBERS AND METHOD FOR EVALUATING REWORKABILITY OF OPTICAL DEVICE CONSTITUENT LAMINATE

TECHNICAL FIELD

The present invention relates to a method for separating two optical device constituent members from an optical device constituent laminate formed by once bonding the two optical device constituent members via a transparent adhesive material, and recycling the optical device constituent members.

BACKGROUND ART

In recent years, in order to enhance visibility of image display devices, a gap between an image display panel such as a liquid crystal display (LCD), a plasma display (PDP), or an electroluminescence display (ELD) and a protective panel or a touch panel member disposed on the front side (viewing side) thereof has been filled with a resin such as an adhesive or a bond to suppress reflection of incident light or light emitting from the display image at an air layer interface.

For example, Patent Document 1 discloses, as a method for producing an image display device constituent laminate having a constitution in which image display device constituent members are laminated on at least one side of a transparent double-sided adhesive sheet, a method including bonding an adhesive sheet subjected to primary crosslinking by UV light to the image display device constituent members, and thereafter irradiating the adhesive sheet by UV light with the image display device constituent members interposed for secondary curing.

When the image display device constituent members are bonded into a single body by the adhesive material as described above, a positional shift or a work error involving air bubbles or foreign substances between the members may occur at the time of bonding work. Thus, the adhesive sheet is required to be repeeled in order to correct this error. Accordingly, there is a case in which the adhesive material used for such a purpose is required to exhibit repeelability (reworkability). In particular, for a laminate made of plate-shaped members having no flexibility, it is not easy to separate after once being bonded. Therefore, when a member for a large screen having difficulty in bonding or an expensive member is bonded, an adhesive material having reworkability has been required.

Conventionally, as the adhesive material having repeelability (reworkability), for instance, Patent Document 2 suggests an adhesive for optical films, which is used a specific acrylic triblock copolymer, and which has excellent adhesion properties and durability without chemical crosslinking, wherein the films can be removed with appropriate peeling strength without adhesive transfer, as a suitable adhesive for the image display devices.

In addition, as a double-sided adhesive sheet which is constituted so as to be repeelable from at least either one of the touch panel or the display surface of the display device, and which is characterized by having optical isotropy, Patent Document 3 discloses a repeelable constitution which is exhibited by having smaller adhesiveness of an adhesive layer on a display device side against a display surface of a display device compared to adhesiveness of an adhesive layer on a touch panel side against a bonding surface of a touch panel.

Further, Patent Document 4 discloses an adhesive sheet which is constituted to have a detachable interface ("internal detachment interface") therein, which is different from bonding surfaces of the adhesive material with the adherends, as a repeelable adhesive material.

CITATION LIST

Patent Document

Patent Document 1: Japanese Patent No. 4971529
Patent Document 2: Japanese Patent No. 5203964
Patent Document 3: Japanese Patent Laid-Open No. 2004-231723
Patent Document 4: International Publication No. WO 2010/137523

SUMMARY OF THE INVENTION

Problem to be Solved by the Invention

When two image display device constituent members are peeled off after once being bonded by using the adhesive material, conventionally, a forcible peeling has been performed by inserting a plate material or a wire material, or the like between the two image display device constituent members. However, in these methods, there is a possibility to damage the image display device constituent members when the image display device constituent members are peeled off.

In addition, when it is assumed that the members are peeled off in the above manner, there is also a case that bonding force of the adhesive material is designed low in advance so as to easily peel the members. However, in such case, since the bonding strength of the adhesive material is low, there is a problem that foaming or the like is likely to occur in the bonded interface.

Further, since it is not easy for the laminate made of plate-shaped members having no flexibility to separate after once being bonded, ease of separation after once being bonded, that is, an adhesive material having "reworkability" may be required in case of that the a member for a large screen having difficulty in bonding or an expensive member is bonded. Therefore, a reworkability evaluation method of the optical device constituent laminate, wherein the "reworkability" of the optical device constituent laminate can be evaluated objectively, has been required.

Thus, the present invention is intended to propose a new method for separating two optical device constituent members from an optical device constituent laminate formed by once bonding the two optical device constituent members via a transparent adhesive material, and recycling the optical device constituent members, as well as a reworkability evaluation method of the optical device constituent laminate.

Means for Solving Problem

The present invention proposes a method for recycling optical device constituent members, wherein an optical device constituent laminate having a constitution in which two optical device constituent members are bonded via a transparent adhesive material which is being softened by heating and crosslinked by light irradiation and being in a pre-crosslinked state is used as a recycle starting material, and comprising following steps: heating at least the transparent adhesive material of the optical device constituent laminate; hanging a linear member along the end edge of the transparent adhesive material of the optical device constituent laminate; dividing the transparent adhesive material by applying a load by the linear member; and producing the two optical device constituent members to which a divided one-side transparent adhesive material adheres.

The present invention additionally proposes a reworkability evaluation method of optical device constituent laminate, wherein an optical device constituent laminate having a constitution in which two optical device constituent members are bonded via a transparent adhesive material which is being softened by heating and crosslinked by light irradiation and being in a pre-crosslinked state is used as an evaluation target, and comprising following steps: heating at least the transparent adhesive material of the optical device constituent laminate; hanging a linear member along the end edge of the transparent adhesive material of the optical device constituent laminate; dividing the transparent adhesive material into two members by applying a load by the linear member; and thereby measuring a weight of the load applied by the liner member and an elapsed time until being divided.

Effect of the Invention

According to the method for recycling the optical device constituent members proposed by the present invention, the optical device constituent members can be recycled in a manner that separating two optical device constituent members from an optical device constituent laminate formed by once bonding the two optical device constituent members via a transparent adhesive material.

In addition, according to the reworkability evaluation method of the optical device constituent laminate proposed by the present invention, ease of separation after once being bonded, that is, an extent of "reworkability" of the optical device constituent laminate can be evaluated objectively, easily and inexpensively.

BRIEF DESCRIPTION OF DRAWINGS

FIG. 1 is a diagram illustrating an example of the optical device constituent laminate as a recycle starting material or an evaluation target, in which (A) is a perspective view thereof, (B) is an exploded perspective view thereof, and (C) is a side view thereof, in the method for recycling the optical device constituent members and the reworkability evaluation method of the optical device constituent laminate according to the present invention.

FIG. 2 is a diagram illustrating a series of flows of an example of the method for recycling the optical device constituent members and the reworkability evaluation method of the optical device constituent laminate according to the present invention, in which (A) illustrates a state of standing the optical device constituent laminate and hanging a linear member thereon, (B) illustrates a state of suspending a weight at the both ends of the linear member respectively, and (C) illustrates a state of being divided the laminate.

FIG. 3 is a diagram illustrating another example of the optical device constituent laminate as the recycle starting material or the evaluation target, in which (A) is a side view thereof, and (B) is a front view thereof, in the method for recycling the optical device constituent members and the reworkability evaluation method of the optical device constituent laminate according to the present invention.

FIG. 4 is a front view illustrating an example of the optical device constituent laminate in a state of being suspended.

FIG. 5 is a side view illustrating an example of the optical device constituent laminate in a state of being suspended.

FIG. 6 is a side view illustrating an example of the optical device constituent laminate in a state of being suspended, in which the linear member is hung thereon and the weight is suspended.

FIG. 7 is a side view illustrating a state that the optical device constituent laminate illustrated in FIG. 6 is divided into two optical device constituent members to which a one-side transparent adhesive material adheres.

FIG. 8 is a diagram illustrating a series of flows of another example of the method for recycling the optical device constituent members and the reworkability evaluation method of the optical device constituent laminate according to the present invention, and is a side view illustrating following steps: standing the optical device constituent laminate vertically; hanging the linear member thereon; suspending the weight at the both ends of the linear member respectively; and dividing the laminate.

FIG. 9 is a diagram illustrating a series of flows of another example of the method for recycling the optical device constituent members and the reworkability evaluation method of the optical device constituent laminate according to the present invention, and is a side view illustrating following steps: standing the optical device constituent laminate vertically; hanging the linear member thereon; suspending the weight at the both ends of the linear member respectively; and dividing the laminate.

FIG. 10 is a step chart illustrating an example of a method that the one-side transparent adhesive material is peeled off from the optical device constituent members to which the one-side transparent adhesive material adheres.

FIG. 11 is a step chart illustrating another example of a method that the one-side transparent adhesive material is peeled off from the optical device constituent members to which the one-side transparent adhesive material adheres.

MODE(S) FOR CARRYING OUT THE INVENTION

Next, the invention will be described on the basis of exemplary embodiments. However, the invention is not limited to the embodiments to be described below.

<Recycle Starting Material and Evaluation Target>

The method for recycling optical device constituent members (referred to as an "present recycling method") and the reworkability evaluation method of the optical device constituent laminate (referred to as an "present reworkability evaluation method") explained as an example of the present embodiment are a method, wherein an optical device constituent laminate 4 having a constitution in which two optical device constituent members 2 and 3 are bonded via a transparent adhesive material (referred to as an "present transparent adhesive material") 1 which is being softened by heating and crosslinked by light irradiation and being in a pre-crosslinked state is used as a recycle starting material or an evaluation target.

(Optical Device Constituent Members)

In the present recycling method and the present reworkability evaluation method, the optical device constituent members 2 and 3 which constitute the optical device constituent laminate 4 as the recycle starting material or the evaluation target may be members for constituting the optical device, and may be members enabling bonding via the adhesive material.

As such the optical devices, for instance, optical devices such as personal computers, mobile terminals (PDAs), gaming machines, televisions (TVs), car navigation systems, touch panels, pen tablets, and solar battery members, can be cited. However, they are not limited to these.

For instance, a touch panel, an image display panel, a surface protection panel, a phase difference film, a polarization film, and the like, can be cited as specific examples of the optical device constituent members 2 and 3, which may be any one of them or a laminate layered by two or more of them in advance. However, they are not limited to these.

(Present Transparent Adhesive Material)

It is preferable that the present transparent adhesive material has a function to bond the optical device constituent members even in a pre-crosslinked state, and has a property of being softened by heating, and has capability of being crosslinked by light irradiation, and is in an uncrosslinked state.

It is preferable that the present transparent adhesive material has a property of being softened by heating at 60 to 100° C.

By having such property, the present transparent adhesive material can be easily separated by heating at 60° C. or more. In addition, the present transparent adhesive material has excellent handleability pertaining to storage stability and cutting in a state of pre-bonding at a normal state, since a shape thereof can be held at a temperature range of less than 60° C.

Meanwhile, if the present transparent adhesive material is softened by heating at a high temperature of more than 100° C., there is a possibility that the image display device constituent members are damaged by heating at more than 100° C.

Thus, from the above points of view, it is preferable that the present transparent adhesive material is softened by heating at 60 to 100° C. More preferably, the present transparent adhesive material has a property of being softened by heating at 63° C. or more or 98° C. or less, and particularly preferably at 65° C. or more or 95° C. or less.

Further, if the present transparent adhesive material is already in a crosslinked state, it is difficult not only to soften the transparent adhesive material by heating, but also to divide the transparent adhesive material by hanging a linear member and pulling at a constant force as described below. Therefore, the present transparent adhesive material in the optical device constituent laminate as the recycle starting material or the evaluation target is required to be in an uncrosslinked state.

In a state that before bonding the optical device constituent members, the present transparent adhesive material may be a sheet shape, or a liquid or gel shape. From the viewpoint of handleability and bonding efficiency, the sheet shape is preferable.

The present transparent adhesive material may be a monolayer or a multilayer.

When the present transparent adhesive material is the multilayer, the present transparent adhesive material may have the above properties, in other words, the present transparent adhesive material may have a function to bond the optical device constituent members even in a pre-crosslinked state, and may have a property of being softened by heating, and may have capability of being crosslinked, and may be in an uncrosslinked state as a whole, and at least one of the layers may have a property of being softened by heating.

Total thickness of the present transparent adhesive material is preferably 50 μm to 1 mm, more preferably 75 μm or more or 500 μm or less.

When the total thickness of the present transparent adhesive material is 50 μm or more, it is preferable on the point that the sheet can not only follow to an unevenness part such as a large printed step, but also has excellent recyclability since the linear member can be easily hung at the end edge of the adhesive material. Meanwhile, when the total thickness is 1 mm or less, the sheet can meet the demand of thinning with respect to the optical device or the like.

Furthermore, from the viewpoint of a higher printed height of the shielding layer on the periphery of a conventional image display device, specifically, from the viewpoint of filling even a step of about 80 μm, the total thickness of the present adhesive material is still more preferably 75 μm or more, particularly further preferably 100 μm or more. Meanwhile, from the viewpoint of meeting the demand of thinning, the total thickness is preferably 500 μm or less, particularly further preferably 350 μm or less.

When the present transparent adhesive material is to have a multilayer constitution, the ratio between the thickness of each of the outermost layers and the thickness of the intermediate layer is preferably 1:1 to 1:20, and further preferably 1:2 to 1:10.

If the thickness of the intermediate layer is in the range described above, it is preferable since the contribution of the thickness of the adhesive material layer in the laminate does not become excessively large, and workability pertaining to cutting and handling does not degrade due to being excessively soft.

In addition, if the outermost layer is in the range described above, it is preferable since followability of unevenness and curved surface does not degrade, and bonding force and wettability to the adherend can be maintained.

It is preferable that the present transparent adhesive material meets the following conditions (1) and (2) in a pre-crosslinked state:

(1) for a sheet with the thickness of 150 μm comprising the pre-crosslinked transparent adhesive material, a shifted length at a temperature of 40° C. with respect to a SUS plate is less than 5 mm in holding force measurement according to JIS-Z-0237;

and (2) for the sheet with the thickness of 150 μm comprising the pre-crosslinked transparent adhesive material, a shifted length at a temperature of 80° C. with respect to a SUS plate is 10 mm or more in holding force measurement according to JIS-Z-0237.

As described in (1), when the shifted length at the temperature of 40° C. is less than 5 mm in the pre-crosslinked state, excellent shape stability and processing suitability can be exhibited in a normal state before the heating.

Further, as described in (2), when the shifted length at the temperature of 80° C. is 10 mm or more in the pre-crosslinked state, in a laminate with not only a comparatively small size of, for instance, 2 to 4 inches, but also a comparatively large size of, for instance, 7 inches or more, a bonded member can be easily separated by heating at 60 to 100° C.

It is preferable that the present transparent adhesive material meets the following conditions (3) and (4) in a pre-crosslinked state:

(3) a 180° peel force is 5 N/cm or more when the sheet with the thickness of 150 μm comprising the pre-crosslinked transparent adhesive material is superposed on a soda lime glass, and the two were roll-crimped by reciprocating a roller of 2 kg one time, and then the adhesive sheet is peeled off from the soda lime glass at a temperature of 23° C., a peel angle of 180°, and a peel rate of 60 mm/min;

and (4) a 180° peel force is less than 2 N/cm when the sheet with the thickness of 150 μm comprising the pre-crosslinked transparent adhesive material is superposed on a soda lime glass, and the two were roll-crimped by reciprocating a roller of 2 kg one time, and then the adhesive sheet is peeled off from the soda lime glass at a temperature of 85° C., a peel angle of 180°, and a peel rate of 60 mm/min.

As described in (3), when the 180° peel force at the temperature of 23° C. is 5 N/cm or more in the pre-crosslinked state, adhesiveness with a peelable degree (referred to as an "tackiness") can be exerted, and by having such tackiness, a positioning for bonding can be easily performed, and it is very convenient on work.

Further, as described in (4), when the 180° peel force at the temperature of 85° C. is less than 2 N/cm in the pre-crosslinked state, for the members after being bonded, excellent repeelability at heating can be imparted.

It is preferable that the present transparent adhesive material meets the following conditions (5) and (6) in a crosslinked state:

(5) a 180° peel force is 5 N/cm or more when the sheet with the thickness of 150 μm comprising the pre-crosslinked transparent adhesive material is superposed on a soda lime glass, and the two were roll-crimped by reciprocating a roller of 2 kg one time, and then the adhesive sheet is peeled off from the soda lime glass at a temperature of 23° C., a peel angle of 180°, and a peel rate of 60 mm/in in a state of that the transparent adhesive material is crosslinked by irradiating light such that light at 365 nm wavelength reached 2,000 mJ/cm$^2$ in the transparent adhesive material;

and (6) a 180° peel force is 3 N/cm or more when the sheet with the thickness of 150 μm comprising the pre-crosslinked transparent adhesive material is superposed on a soda lime glass, and the two were roll-crimped by reciprocating a roller of 2 kg one time, and then the adhesive sheet is peeled off from the soda lime glass at a temperature of 85° C., a peel angle of 180°, and a peel rate of 60 mm/min in a state of that the transparent adhesive material is crosslinked by irradiating light such that light at 365 nm wavelength reached 2,000 mJ/cm$^2$ in the transparent adhesive material.

As described in (5), when the 180° peel force at the temperature of 23° C. is 5 N/cm or more in the crosslinked state, it is preferable since reliability with respect to a peeling or the like of the bonded laminate in a normal state can be secured.

Further, as described in (6), when the 180° peel force at the temperature of 85° C. is 3 N/cm or more in the crosslinked state, a laminate having excellent durability can be provided.

(Present Transparent Adhesive Material and Adhesive Composition)

Since the present transparent adhesive material is softened by heating in a pre-photo-curing state, and preferably has fluidity, the bonded part can be easily separated by heating even when it is necessary to peel off the once bonded laminate due to a work error or the like.

Therefore, with the present transparent adhesive material, there is no need to reduce a peel force of the adhesive layer, and both high reliability with respect to peeling and foaming after bonding of the members, and repeelability can be obtained.

A preferable adhesive composition to form such transparent adhesive material will be described as follows.

<Present Recycling Method>

The present recycling method is a method which is provided with a step for heating a transparent adhesive material 1 of the optical device constituent laminate 4 as a recycle starting material, hanging a linear member 5 along the end edge of the transparent adhesive material 1 of the optical device constituent laminate 4, dividing the transparent adhesive material 1 by applying a load by the linear member 5, thereby producing two optical device constituent members 2 and 3 to which a divided one-side transparent adhesive materials 1A adheres.

Incidentally, either the step of hanging the linear member 5 or the step of heating the transparent adhesive material 1 may be performed first, or the both may be performed simultaneously. Also, either the step of applying the load by the linear member 5 or the step of heating the transparent adhesive material 1 may be performed first, or the both may be performed simultaneously.

In the step of hanging the linear member 5, it is preferable to follow these steps: standing the optical device constituent laminate 4 used as the recycle starting material; heating the transparent adhesive material 1 of the optical device constituent laminate 4; and hanging the linear member 5 along the end edge of the transparent adhesive material 1 of the optical device constituent laminate 4.

The method of standing the optical device constituent laminate 4 used as the recycle starting material may be an arbitrary method. For instance, the optical device constituent laminate 4 may be fixed by supporting from both sides so as to stand vertically as illustrated in FIG. 2 (A) to (C), or may be suspended so as to be vertical posture as illustrated in FIGS. 4 and 6.

In so doing, for instance, as illustrated in FIG. 2 (A) to (C), by using a pedestal 6 having a plurality of posts 6A, 6A . . . which are stood on upper surface at specific intervals, the optical device constituent laminate 4 can be fixed by the following steps: standing the optical device constituent laminate 4 vertically, placing the optical device constituent laminate 4 in between the posts 6A and 6A on upper surface of the pedestal 6, and supporting the optical device constituent laminate 4 in between the posts 6A and 6A. However, the present invention is not intended to be limited to such method.

Here, the supporting method is arbitrary if the optical device constituent laminate 4 can be stood. For instance, it may be supported with a supporting member such as bookends or may be supported mechanically, or the other method may be employed.

Meanwhile, as illustrated in FIGS. 3 to 5, the optical device constituent laminate 4 can also be stood vertically by the following steps: winding belts 7 and 7 around both right and left sides of the optical device constituent laminate 4 respectively; hanging the belts 7 and 7 on hooks 8 and 8; and suspending the optical device constituent laminate 4.

In so doing, to be able to suspend the optical device constituent members 2 and 3 even after being divided, the optical device constituent member 3 which has a larger size is suspended by winding the belts 7 and 7 around both right and left sides thereof respectively and by hanging the belts 7 and 7 on the hooks 8 and 8 as described above. Meanwhile, the optical device constituent member 2 which has a smaller size is preferably supported by sticking support tapes 9 on the side face of both right and left sides of the optical device constituent member 2 respectively and by hanging the support tapes 9 on hooks 10 and 10.

The support tape 9 is preferably an adhesive tape having heat resistance. For instance, an adhesive tape having a constitution in which a silicon series adhesive material is laminated on a glass cross substrate can be indicated as examples.

Incidentally, when the optical device constituent laminate 4 is stood vertically, upper end edges of the optical device constituent members 2 and 3 and an upper edge of the transparent adhesive material 1 may be flat on one face, or the upper edge of the transparent adhesive material 1 may be lower than the upper end edges of the optical device constituent members 2 and 3, and may be a concave groove.

As the method of heating at least the transparent adhesive material 1 of the optical device constituent laminate 4, for instance, a method of heating the entire optical device constituent laminate 4 by putting into a heating apparatus such as a heating furnace, a method of heating the optical device constituent laminate 4 partially by a dryer or a heat gun or the like, and a method of heating the transparent adhesive material 1 locally by an electrical resistive heating of the linear member 5 per se, can be cited. Among them, the method of heating the entire optical device constituent laminate is preferable in terms of simplicity of the work. However, the present invention is not intended to be limited to such heating method.

The temperature at which at least the transparent adhesive material 1 of the optical device constituent laminate 4 is heated is preferably 60 to 100° C. This is because, when it is heated at 60° C. or more, the transparent adhesive material 1 can be easily divided by being softened, meanwhile, when it is heated at 100° C. or less, it is unlikely to impart a thermal damage to the optical device constituent members 2 and 3.

As the method of standing the optical device constituent laminate 4, hanging the linear member 5 along the end edge 1a of the transparent adhesive material 1 located at the upper end edge 4a of the optical device constituent laminate 4, and applying the load by the linear member 5, for instance, as illustrated in FIG. 2 (A) to (C) or FIGS. 3 to 6, a method of hanging the linear member 5 so as to be superposed along the end edge 1a of the transparent adhesive material 1 located at the upper end edge 4a of the optical device constituent laminate 4, hanging the both ends of the linear member 5 lowered down, and pulling the both ends to the vertically downward direction at a constant force, can be cited.

By hanging the linear member 5 and pulling to the vertically downward direction at the constant force in the state of that the transparent adhesive material 1 is softened by heating, the linear member 5 is moved down gradually in the layer of the transparent adhesive material 1, thereby the transparent adhesive material 1 can be divided without applying excessive force.

Herein, as the method of pulling the both ends of the linear member 5 to the vertically downward direction at the constant force, for instance, it may be pulled mechanically, or it may be pulled by suspending weights 11 at the both ends of the linear member 5 as illustrated, for instance, in FIGS. 2 (B) and (C) or FIG. 6. According to the latter method, since it is sufficient just to leave the linear member 5 by suspending the weights 11, the optical device constituent laminate 4 can be recycled easily and inexpensively without use of any special machinery or apparatus.

Further, as illustrated, for instance, in FIGS. 8 and 9, the linear member 5 may be pulled to the vertically downward direction at a constant force as following steps: fixing one end of the linear member 5 at a fixed wall such as a frame; hanging the linear member 5 along the end edge 1a of the transparent adhesive material 1 located at the upper end face 4a of the optical device constituent laminate 4; hanging another end of the linear member 5 lowered down; and suspending the weight 11 at the another end.

In so doing, the linear member 5 may be hung at a corner of the other end side of the transparent adhesive material 1 by fixing one side of the linear member 5 at a fixed wall position located higher than the upper end face 4a of the optical device constituent laminate 4 as illustrated in FIG. 8, or the linear member 5 may be hung at the end edge 1a of the transparent adhesive material 1 to be very close by fixing one side of the linear member 5 at a fixed wall position located lower than the upper end face 4a of the optical device constituent laminate 4 as illustrated in FIG. 9.

(Linear Member)

As the liner member 5, for instance, a string-shaped member comprising a fiber, a string-shaped member comprising a synthetic resin such as a fishing line, a metallic wire such as a piano wire, a string-shaped member comprising a carbon fiber, or the like, can be cited. However, they are not limited to these.

Among them, from the viewpoint that the optical device constituent members are not damaged, the string-shaped member comprising a fiber, the string-shaped member comprising a synthetic resin such as a fishing line, the string-shaped member comprising a carbon fiber, or the like are preferable.

A diameter of the liner member 5 is preferably 0.1 to 1.5 times the thickness of the transparent adhesive material 1, more preferably 0.3 times or more or 1.0 times or less the thickness of the transparent adhesive material 1, and even more preferably 0.5 times or more or 0.9 times or less the thickness of the transparent adhesive material 1.

(Dividing)

As described above, by standing the optical device constituent laminate 4, hanging the linear member 5 at the end edge 1a of the transparent adhesive material 1 of the optical device constituent laminate 4, heating at least the transparent adhesive material 1 of the optical device constituent laminate 4, and pulling the linear member 5 downward, a layer comprising the transparent adhesive material 1 can be divided into two members by the linear member 5 as illustrated in FIG. 2 (C) or 7, and can be separated into two optical device constituent members 2 and 3 to which one-side transparent adhesive materials 1A and 1A adhere respectively.

(Separation of Transparent Adhesive Material)

Next, as illustrated in FIG. 10, by peeling the one-side transparent adhesive material 1A from the optical device constituent member 2 (3) to which the one-side transparent adhesive material 1A adheres, the optical device constituent member 2 (3) can be recycled.

In so doing, the method to peel the one-side transparent adhesive material 1A from the optical device constituent member 2 (3) to which the one-side transparent adhesive material 1A adheres is arbitrary. For instance, it can be peeled off forcibly by using a tool such as a spatula, or can be peeled off chemically by using a solvent. Further, as illustrated in FIG. 10 (A) to (C), it is sufficient to peel off the one-side transparent adhesive material 1A together with the adhesive material 12 after superposing and bonding an adhesive material 12 on the one-side transparent adhesive material 1A of the optical device constituent member 2 (3) to which the one-side transparent adhesive material 1A adheres.

If the adhesive material 12 is an adhesive material having rubber elasticity, as illustrated in FIG. 10 (C), by pulling the adhesive material 12 to the parallel direction with the planar direction, that is, to the shear direction of the adhesion interface between the one-side transparent adhesive material and the optical device constituent members, the one-side transparent adhesive material 1A can be peeled off together with the adhesive material 12.

Herein, before or after bonding the adhesive material 12, the adhesive material 12 and the one-side transparent adhesive material 1A may be peeled off from the optical device constituent member 2 (3) while the one-side transparent adhesive material 1A is irradiated by UV light and cured if necessary. By curing the one-side transparent adhesive material 1A before removing the one-side transparent adhesive material 1A, it is effective for decreasing the adhesive transfer on the surface of the optical device constituent member 2 (3).

As illustrated in FIG. 11, after superposing and bonding a sheet or film shaped support 13 having no rubber elasticity on the one-side transparent adhesive material 1A of the optical device constituent member 2 (3) to which the one-side transparent adhesive material 1A adheres, the one-side transparent adhesive material 1A may be peeled off from the optical device constituent member 2 (3) together with the support 13. In this case, the one-side transparent adhesive material 1A may also be irradiated by UV light and cured if necessary.

Here, if the support 13 has a bonding force with respect to the one-side transparent adhesive material 1A which is at least higher than the peel force of the one-side transparent adhesive material 1A with respect to the optical device constituent member 2 (3), any material can be used as the support 13. For instance, the material may be a PET film, or a support with adhesive such as a packing tape.

After peeling the one-side transparent adhesive material 1A from the optical device constituent member 2 (3), the adhesive material component remained on the peeled surface of the optical device constituent member 2 (3) may be removed by dissolving with an organic solvent such as ethanol. The optical device constituent member 2 (3) can be thus used as a new material.

<Present Reworkability Evaluation Method>

The present reworkability evaluation method, wherein the optical device constituent laminate 4 is used as an evaluation target, comprises following steps: heating the transparent adhesive material 1; dividing the transparent adhesive material 1 of the optical device constituent laminate 4 into two members by applying a load by the linear member 5 in the same manner as the above recycling method; and measuring a weight of the load applied by the liner member 5 and an elapsed time since the load was applied by the liner member 5 until being divided. Thereby, the reworkability of the optical device constituent laminate can be evaluated on the basis of these values.

For instance, the reworkability of the optical device constituent laminate can be evaluated on the basis of the force to pull the liner member 5 to the vertically downward direction and the product of the elapsed time until being divided.

Further, the reworkability of the optical device constituent laminate can be evaluated in the manner that, for instance, a target time required for dividing is set to 15 minutes, and it is judged as a pass if the optical device constituent laminate can be divided within the target time.

[Adhesive Composition]

As the present adhesive composition 1, that is, the adhesive composition to form the transparent adhesive material having adhesiveness even in an uncrosslinked state, and which is softened by heating at 60 to 100° C. and crosslinked by light irradiation, the following adhesive compositions A and B can be cited as preferred examples.

The present transparent adhesive material can be produced by forming an adhesive material layer from the adhesive compositions A and B and laminating the other adhesive material layer or a photo-curing layer if necessary.

However, the adhesive composition to form the present transparent adhesive material is not limited to the following adhesive compositions A and B.

Incidentally, when the present transparent adhesive material is to be made into a multilayered transparent double-sided adhesive sheet, the present transparent adhesive material is preferably formed using the adhesive composition, for instance the adhesive composition A or B, since it is preferable that the outermost layer is provided with unevenness followability and anti-bubble reliability as in the case of the monolayer described above.

Meanwhile, it is preferable that the intermediate layer has light permeability to an extent that does not inhibit secondary curing reaction of outermost layers and has properties that elevate cuttability and handleability without losing transparency, since it does not contribute to the bonding of the image display device constituent members.

The species of the base polymer forming the intermediate layer is not limited in particular if it is a transparent resin. The base polymer forming the intermediate layer may be the same resin as or a different resin from that of the outermost layers. Among them, from such points of view as securing transparency and ease of production, and further to prevent refraction of light at the layer interface, using an identical acrylic series resin to the base polymer of the outermost layer is preferable.

The intermediate layer and the other resin layer may have or may not have active energy ray curability. For instance, the intermediate layer and the other resin layer may be formed so as to be cured by UV crosslinking, or may be formed so as to be cured by heat. In addition, it may be formed so as not to be post-cured in particular. However, when tightness of contact with the outermost layers or the like is considered, it is preferable to form so as to be post-cured, and particularly preferable to form so as to be UV crosslinked.

In so doing, since light transmittance is decreased if the content in crosslinking initiator becomes large, it is preferable that the UV crosslinking agent is contained at a lower content rate than the content rate in the outer layer of the crosslinking initiator in the intermediate layer.

When the present transparent adhesive material is to be made into a multilayered transparent double-sided adhesive sheet, as a layered constitution, specifically, for instance, a two-layer by two-kind constitution in which the adhesive composition A or B and the other adhesive composition are laminated, a three-layer by two-kind constitution in which the adhesive composition A or B is disposed on the front and the back via the intermediate resin layer, a three-layer by three-kind constitution in which the adhesive composition A or B, the intermediate resin composition, and the other adhesive composition are laminated in this order, or the like, can be cited.

<Adhesive Composition A>

As the adhesive composition A, a resin composition containing an acrylic series copolymer (A1) which comprises a graft copolymer having a macromonomer as branch component, a crosslinking agent (B1), and a photopolymerization initiator (C1), can be cited.

Incidentally, for the detailed composition and properties of the adhesive composition A, the contents described in the paragraphs [0018] to [0091] of JP-A No. 2014-045936 are cited.

<Acrylic Series Copolymer (A1)>

The acrylic series copolymer (A1) is a graft copolymer having a macromonomer as branch component.

(Stem Component)

It is preferable that stem component of the acrylic series copolymer (A1) is constituted by a copolymer component containing a repeating unit derived from (meth)acrylic acid ester.

It is preferable that a glass transition temperature of the copolymer which constitutes the stem component of the acrylic series copolymer (A1) is −70 to 0° C.

Here, the glass transition temperature of the copolymer component which constitutes the stem component means a glass transition temperature of a polymer obtained by copolymerization of only a monomer component which composes the stem component of the acrylic series copolymer (A1). Specifically, the glass transition temperature of the copolymer component which constitutes the stem component means a value calculated from a glass transition temperature of a polymer obtained from a homopolymer of the each copolymer component and a constitution ratio, by a FOX's calculation formula.

Incidentally, the FOX's calculation formula is a following formula, and the glass transition temperature of the copolymer component which constitutes the stem component is determined by using the value described in Polymer Handbook (J. Brandrup, Interscience, 1989).

$$1/(273+Tg) = \Sigma(Wi/(273+Tgi))$$

[where Wi represents a weight fraction of a monomer i, Tgi represents a Tg (° C.) of a homopolymer of the monomer i]

Since the glass transition temperature of the copolymer component which constitutes the stem component of the acrylic series copolymer (A1) influences flexibility of the adhesive composition A at room temperature and wettability of the adhesive composition A with respect to an adherend, that is, adhesiveness, the glass transition temperature is preferably −70 to 0° C., more preferably −65° C. or more or −5° C. or less, and particularly preferably −60° C. or more or −10° C. or less, in order for the adhesive composition A to obtain suitable adhesiveness (tackiness) at room temperature.

However, even when the glass transition temperature of the copolymer component is the same temperature, viscoelasticity can be adjusted by adjusting the molecular weight. For instance, it can be further softened by lowering molecular weight of the copolymer component.

As (meth)acrylic acid ester monomers which comprise the stem component of the acrylic series copolymer (A1), for instance, 2-ethylhexyl acrylate, n-octyl acryte, isooctyl acrylate, n-butyl acrylate, ethyl acrylate, methyl methacrylate, methyl acrylate, and the like, can be cited. As such (meth) acrylic acid ester monomers having a hydrophilic group, an organic functional group, or the like, hydroxyethyl acrylate, hydroxyethyl methacrylate, hydroxypropyl acrylate, hydroxypropyl methacrylate, acrylic acid, methacrylic acid, glycidyl acrylate, acrylamide, N,N-dimethylacrylamide, acrylonitrile, methacrylonitrile, and the like, can also be used.

In addition, various vinyl monomers such as vinyl acetate, alkyl vinyl ether and hydroxyalkyl vinyl ether, which are copolymerizable with the acrylic monomer or the methacrylic monomer, can also be appropriately used.

Furthermore, it is preferable that the stem component of the acrylic series copolymer (A1) contains a hydrophobic (meth)acrylate monomer and a hydrophilic (meth)acrylate monomer as a constitutional unit.

When the stem component of the acrylic series copolymer (A1) is constituted solely by the hydrophobic monomer, a tendency to be a hygrothermal whitening is observed, thereby it is preferable to prevent the hygrothermal whitening by introducing the hydrophilic monomer to the stem component as well.

Specifically, as the stem component of the acrylic series copolymer (A1), a copolymer component obtained by the random copolymerization of the hydrophobic (meth)acrylate monomer, the hydrophilic (meth)acrylate monomer, and the polymerizable functional group of the terminal of the macromonomer, can be cited.

Herein, as the hydrophobic (meth)acrylate monomers above, for instance, n-butyl (meth)acrylate, n-hexyl (meth)acrylate, n-octyl (meth)acrylate, n-nonyl (meth)acrylate, n-decyl (meth)acrylate, 2-ethylhexyl (meth)acrylate, 2-methylhexyl (meth)acrylate, isooctyl (meth)acrylate, isononyl (meth)acrylate, isodecyl (meth)acrylate, ethyl (meth)acrylate, n-propyl (meth)acrylate, isopropyl (meth) acrylate, t-butyl (meth)acrylate, isobutyl (meth)acrylate, isobornyl (meth)acrylate, cyclohexyl (meth)acrylate, dicyclopentenyloxyethyl (meth)acrylate, methyl methacrylate, vinyl acetate, and the like, can be cited.

As the hydrophilic (meth)acrylate monomers above, for instance, methyl acrylate, (meth)acrylic acid, tetrahydrofurfuryl (meth) acrylate, 2-hydroxyethyl (meth)acrylate, methoxy polyethylene glycol (meth)acrylate, 2-(meth)acryloyloxyethyl succinate, 2-(meth)acryloyloxyethyl phthalate, 2-(meth)acryloyloxypropyl hexahydrophthalate, N,N-dimethylacrylamide, hydroxyethyl acrylamide, and the like, can be cited.

(Branch Component: Macromonomer)

It is important that a macromonomer is introduced into the acrylic series copolymer (A1) as branch component of the graft copolymer, and the acrylic series copolymer (A1) contains a repeating unit derived from the macromonomer.

The macromonomer is a high-molecular monomer having the polymerizable functional group of the terminal and the high-molecular weight skeleton component.

It is preferable that a glass transition temperature (Tg) of the macromonomer is higher than that of the copolymer component which constitutes the acrylic series copolymer (A1).

Specifically, since the glass transition temperature (Tg) of the macromonomer influences a heating and melting temperature (hot-melting temperature) of the adhesive composition A, the glass transition temperature (Tg) of the macromonomer is preferably 30 to 120° C., more preferably 40° C. or more or 110° C. or less, and further preferably 50° C. or more or 100° C. or less.

With such glass transition temperature (Tg), excellent processability and storage stability can be retained by adjusting the molecular weight, and the macromonomer can be adjusted to hot-melt at near 80° C.

The glass transition temperature of the macromonomer, which means a glass transition temperature of the macromonomer per se, can be measured by a differential scanning calorimeter (DSC).

In addition, it is also preferable to adjust the content of the macromonomer, since a state as if the macromonomer is physically crosslinked, as an adhesive composition, by pulling the branch components together can be maintained at room temperature, and moreover, fluidity can be obtained by melting the physical crosslinking after being heated to the appropriate temperature.

From this point of view, the macromonomer is preferably contained in the acrylic series copolymer (A1) at a proportion of 5 to 30% by mass. More preferably, it is contained at a proportion of 6% by mass or more or 25% by mass or less, and even more preferably at a proportion of 8% by mass or more or 20% by mass or less.

It is preferable that a high-molecular weight skeleton component of the macromonomer is constituted by an acrylic series polymer or a vinyl series polymer.

As the high-molecular weight skeleton component of the macromonomer, for instance, a copolymer of polystyrene, styrene, and acrylonitrile, poly(t-butylstyrene), poly(α-methylstyrene), polyvinyl toluene, polymethyl methacrylate, and the like, can be cited.

As the terminal polymerizable functional group of the macromonomer, for instance, methacryloyl group, acryloyl group, and vinyl group, and the like, can be cited.

(Physical Properties of Acrylic Series Copolymer (A1))

The complex viscosity of the acrylic series copolymer (A1) at a temperature of 130° C. and a frequency of 0.02 Hz is preferably 100 to 800 Pa·s, more preferably 150 to 700 Pa·s, and further preferably 170 to 600 Pa·s.

Since the complex viscosity of the acrylic series copolymer (A1) at the temperature of 130° C. influences fluidity of the adhesive composition A when the transparent double-sided adhesive material is used by hot-melting, if such complex viscosity is 100 to 800 Pa·s, excellent hot-melting suitability can be provided.

In order to adjust the complex viscosity of the acrylic series copolymer (A1) to be in the range described above, for instance, a method for adjusting the glass transition temperature of the copolymer component which constitutes the stem component of the acrylic series copolymer (A1), can be cited. The adjustment method of viscoelasticity by adjusting the glass transition temperature so as to be preferably in a range of −70 to 0° C., more preferably −65° C. or more or −5° C. or less, and even more preferably −60° C. or more or −10° C. or less, and by adjusting the molecular weight of the copolymer component, can be cited. However, the adjustment method is not limited to these methods.

<Crosslinking Agent (B1)>

As a crosslinking agent (B1), for instance, a crosslinking agent comprising an epoxy crosslinking agent, an isocyanate crosslinking agent, an oxetane compound, a silane compound, an acrylic compound, or the like, can be appropriately selected. Among them, from the viewpoint of reactivity and the strength of the obtained cured product, a polyfunctional (meth)acrylate having three or more (meth)acryloyl groups is preferable.

By crosslinking the crosslinking agent (B1) in the adhesive material after the image display device constituent members are bonded into a single body, the sheet loses hot-melting properties, and instead of that, high cohesive force can be exerted under high temperature environment, and excellent anti foaming reliability can be obtained.

As such polyfunctional (meth)acrylate, for instance, in addition to ultraviolet-curable polyfunctional monomers such as 1,4-butanediol di(meth)acrylate, glycerin di(meth)acrylate, glyceringlycidyl ether di(meth)acrylate, 1,6-hexanediol di(meth)acrylate, 1,9-nonanediol di(meth)acrylate, tricyclodecanedimethanol di(meth)acrylate, bisphenol A polyethoxy di(meth)acrylate, bisphenol A polypropoxy di(meth)acrylate, bisphenol F polyethoxy di(meth)acrylate, ethylene glycol di(meth)acrylate, trimethylolpropane trioxyethyl (meth)acrylate, ε-caprolactone-modified tris(2-hydroxyethyl)isocyanurate tri(meth)acrylate, pentaerythritol tri(meth)acrylate, propoxylated pentaerythritol tri(meth)acrylate, ethoxylated pentaerythritol tri(meth)acrylate, pentaerythritol tetra(meth)acrylate, propoxylated pentaerythritol tetra(meth)acrylate, ethoxylated pentaerythritol tetra(meth)acrylate, dipentaerythritol hexa(meth)acrylate, polyethylene glycol di(meth)acrylate, tris(acryloxyethyl)isocyanurate, pentaerythritol tetra(meth)acrylate, dipentaerythritol hexa(meth)acrylate, dipentaerythritol penta(meth)acrylate, tripentaerythritol hexa(meth)acrylate, tripentaerythritol penta(meth)acrylate, hydroxy pivalic acid neopentyl glycol di(meth)acrylate, di(meth)acrylate of ε-caprolactone adduct of hydroxy pivalic acid neopentyl glycol, trimethylolpropane tri(meth)acrylate, trimethylolpropanepolyethoxy tri(meth)acrylate, and ditrimethylolpropane tetra(meth)acrylate; polyfunctional acrylic oligomers such as polyester (meth)acrylate, epoxy (meth)acrylate, urethane (meth)acrylate and polyether (meth)acrylate; can be cited.

Among the above, from the viewpoints of improving tightness of contact with respect to the adherend and the effect of suppressing hygrothermal whitening, a polyfunctional monomer or an oligomer containing a polar functional group such as a hydroxyl group is preferable.

Among them, it is more preferable to use a polyfunctional (meth)acrylic acid ester having a hydroxyl group.

Accordingly, from the viewpoint of preventing the hygrothermal whitening, it is preferable to contain the hydrophobic acrylate monomer and the hydrophilic acrylate monomer as stem component of the acrylic series copolymer (A1), that is, the graft copolymer, and furthermore, it is preferable to use the polyfunctional (meth)acrylic acid ester having the hydroxyl group as the crosslinking agent (B1).

The content of the crosslinking agent (B1) is not limited in particular. As a guide, the content is preferably at a proportion of 0.5 to 20 parts by mass, more preferably 1 part by mass or more or 15 parts by mass or less, and even more preferably 2 parts by mass or more or 10 parts by mass or less, with respect to 100 parts by mass of the acrylic series copolymer (A1).

By containing the crosslinking agent (B1) at the above range, both the shape stability of the present transparent adhesive material in an uncrosslinked state and the anti-foaming reliability of the adhesive material in a crosslinked state can be obtained. However, the ratio may be out of such ranges depending on the balance with other elements.

<Photopolymerization Initiator (C1)>

A photopolymerization initiator (C1) fulfills a function as a reaction initiating aid in a crosslinking reaction of the crosslinking agent (B1). A currently well-known initiator can be suitably used as the photopolymerization initiator. In particular, a photopolymerization initiator which responds to UV light with a wavelength of 380 nm or less is preferable in terms of the controllability of the crosslinking reaction.

The photopolymerization initiator is roughly classified into two types by the radical generation mechanism: a cleavage type photopolymerization initiator that can generate a radical by cleavage and decomposition of a single bond of the photopolymerization initiator per se; and a hydrogen abstraction type photopolymerization initiator in which a photoexcited initiator and a hydrogen donor in the system can form an excited complex to allow hydrogen of the hydrogen donor to be transferred.

Of these, the cleavage type photopolymerization initiator is decomposed and converted into another compound in radical generation by light irradiation, and, if once excited, it does not have a function as a reaction initiator. For this reason, the cleavage type photopolymerization initiator is preferable since it does not remain as an active species in the adhesive material after the completion of the crosslinking reaction and it is not concerned that unexpected light deterioration of the adhesive material is brought about.

Meanwhile, the hydrogen abstraction type photopolymerization initiator is useful since it does not generate a decomposed product such as the cleavage type photopolymerization initiator at the time of the radical generation reaction by irradiation with an active energy ray such as UV light, and thus it is hardly converted into a volatile component after the completion of the reaction, and damage of the adherend can be decreased.

As the cleavage type photoinitiator, for instance, 2,2-dimethoxy-1,2-diphenylethane-1-one, 1-hydroxycyclohexyl phenyl ketone, 2-hydroxy-2-methyl-1-phenyl-propane-1-one, 1-(4-(2-hydroxyethoxy)phenyl)-2-hydroxy-2-methyl-1-propan-1-one, 2-hydroxy-1-[4-{4-(2-hydroxy-2-methyl-propionyl)benzyl}phenyl]-2-methyl-propan-1-one, oligo(2-hydroxy-2-methyl-1-(4-(1-methylvinyl)phenyl)propanone), methyl phenylglyoxylate, 2-benzyl-2-dimethylamino-1-(4-morpholinophenyl)butane-1-one, 2-methyl-1-[4-(methylthio)phenyl]-2-morpholinopropane-1-one, 2-(dimethylamino)-2-[(4-methylphenyl)methyl]-1-[4-(4-morpholinyl)phenyl]-1-butanone, bis(2,4,6-trimethylbenzoyl)-phenylphosphine oxide, 2,4,6-trimethylbenzoyldiphenylphosphine oxide, or any derivative thereof, can be cited.

As the hydrogen abstraction type photoinitiator, for instance, benzophenone, 4-methyl-benzophenone, 2,4,6-trimethylbenzophenone, 4-phenylbenzophenone, 3,3'-dimethyl-4-methoxybenzophenone, methyl 2-benzoylbenzoate, methyl benzoylformate, bis(2-phenyl-2-oxoacetic acid)oxy-bis-ethylene, 4-(1,3-acryloyl-1,4,7,10,13-penta-oxo-tridecyl)benzophenone, thioxanthone, 2-chlorothioxanthone, 3-methylthioxanthone, 2,4-dimethylthioxanthone, 2-methylanthraquinone, 2-ethylanthraquinone, 2-tert-butyl-anthraquinone, 2-aminoanthraquinone, or any derivative thereof, can be cited.

However, the photopolymerization initiator is not limited to the substances mentioned above. Any one kind of the cleavage type photopolymerization initiator and the hydrogen abstraction type photopolymerization initiator may be used or both of them may be used in combination for the adhesive composition A.

The content of the photopolymerization initiator (C1) is not limited in particular. As a guide, the content is preferably at a proportion of 0.1 to 10 parts by mass, more preferably 0.5 part by mass or more or 5 parts by mass or less, and even more preferably 1 part by mass or more or 3 parts by mass or less, with respect to 100 parts by mass of the acrylic series copolymer (A1).

By having the content of the photopolymerization initiator (C1) in the range described above, appropriate reaction sensitivity with respect to the active energy ray can be obtained.

<Other Components (D1)>

The adhesive composition A may contain known components which are blended into an ordinary adhesive composition, as a component other than the above. For example, various kinds of additives such as a tackifying resin, an antioxidant, a light stabilizer, a metal deactivator, an anti-aging agent, and a moisture absorbent can be appropriately contained, if necessary.

In addition, a reaction catalyst (tertiary amine type compound, quaternary ammonium type compound, tin laurate compound, or the like) may also be appropriately contained, if necessary.

<Adhesive Composition B>

As the adhesive composition B, a resin composition, which is formed by copolymerization of a monomer a1 having a glass transition temperature of less than 0° C., a monomer a2 having a glass transition temperature of 0° C. or more and less than 80° C., and a monomer a3 having a glass transition temperature of 80° C. or more in a mole ratio of a1:a2:a3=10 to 40:90 to 35:0 to 25, containing a base polymer (A2) which comprises a (meth)acrylic acid ester copolymer or a vinyl copolymer having a weight average molecular weight of 50,000 to 400,000, a crosslinking agent (B2), and a photopolymerization initiator (C2), can be cited.

Incidentally, for the detailed composition and properties of the adhesive composition B, the contents described in the paragraphs [0014] to [0072] of JP-A No. 2014-32074 are cited.

Here, the base polymer means a resin which is contained in the adhesive composition B as a main component. Although the specific content is not defined, as a guide, the content proportion of the resin is 50% by mass or more, particularly 80% by mass or more, and among them, 90% by mass or more (including 100%, by mass) with respect to resins contained in the adhesive composition B (when two or more base polymer is present, sum of these contents corresponds to the content mentioned above).

<Base Polymer (A2)>

The base polymer (A2) is preferably a (meth)acrylic acid ester copolymer or a vinyl copolymer.

From the viewpoint of achieving both the shape stability at room temperature and the hot-melting properties, a weight average molecular weight of the (meth)acrylic acid ester copolymer or the vinyl copolymer is preferably 50,000 to 400,000, more preferably 60,000 or more or 350,000 or less, and more preferably 70,000 or more or 300,000 or less.

In the acrylic acid ester series copolymer, the physical properties such as the glass transition temperature (Tg) and the molecular weight can be appropriately adjusted by selecting the species, composition ratio, furthermore, the polymerization conditions, and the like, of the acrylic monomer or the methacrylic monomer used to adjust this.

At this time, as acrylic monomers constituting the acrylic acid ester copolymer, for instance, 2-ethylhexyl acrylate, n-octylacryte, isooctyl acrylate, n-butyl acrylate, ethyl acrylate, and the like can be cited as the main raw materials.

Aside from these, a (meth)acrylic monomer having various functional groups may be copolymerized with the acrylic monomer, according to such purposes as conferring cohesive force, conferring polarity, and the like.

As the (meth)acrylic monomer having the functional groups, for instance, methyl methacrylate, methyl acrylate, hydroxyethyl acrylate, acrylic acid, glycidyl acrylate, N-substituted acrylamide, acrylonitrile, methacrylonitrile, fluorine-containing alkyl acrylate, organo-siloxy group-containing acrylate, and the like, can be cited.

Meanwhile, as the vinyl copolymer, a vinyl copolymer, which is suitably formed by polymerization of various vinyl monomers, such as vinyl acetate which is copolymerizable with the acrylic monomers and the methacrylic monomers above, alkylvinyl ether, and hydroxy alkylvinyl ether, can be cited.

It is preferable that the base polymer (A2) of the present adhesive sheet is a (meth)acrylic acid ester copolymer or a vinyl copolymer which is formed by copolymerization of a monomer A having a glass transition temperature of less than 0° C., a monomer B having a glass transition temperature of 0° C. or more and less than 80° C., and a monomer C having a glass transition temperature of 80° C. or more in a mole ratio of A:B:C=10 to 40:90 to 35:0 to 25.

Here, each of the glass transition temperature (Tg) of the monomer A, B and C means a glass transition temperature (Tg) when a polymer is produced from the monomer (homopolymerized).

The monomer A is preferably a (meth)acrylic acid ester monomer having an alkyl group structure which has, for instance, a side chain of 4 or more carbon numbers.

In so doing, the side chain of 4 or more carbon numbers may comprise a straight chain or a branched carbon chain.

More specifically, the monomer A is preferably a (meth)acrylic acid ester monomer having a straight chain alkyl group structure of 4 to 10 carbon numbers, or a (meth)acrylic acid ester monomer having a branched alkyl group structure of 6 to 18 carbon numbers.

Herein, as the "(meth)acrylic acid ester monomer having a straight chain alkyl group structure of 4 to 10 carbon numbers", n-butyl acrylate, n-hexyl acrylate, n-octyl acrylate, n-nonyl acrylate, n-decyl acrylate, and the like, can be cited.

Meanwhile, as the "(meth)acrylic acid ester monomer having a branched chain alkyl group structure of 6 to 18 carbon numbers", 2-ethylhexyl acrylate, 2-ethylhexyl methacrylate, 2-methylhexyl acrylate, isooctyl acrylate, isononyl acrylate, isodecyl acrylate, isodecyl methacrylate, and the like, can be cited.

The monomer B is preferably a (meth)acrylic acid ester monomer of 4 or less carbon numbers, a (meth)acrylic acid ester monomer having a cyclic skeleton in the side chain, a vinyl monomer of 4 or less carbon numbers, or a vinyl monomer having a cyclic skeleton in the side chain.

Among them, the monomer B is more preferably a vinyl monomer in which the carbon number of the side chain is 4 or less.

Herein, as the "(meth)acrylic acid ester monomer of 4 or less carbon numbers", methyl acrylate, ethyl methacrylate, n-propyl acrylate, n-propyl methacrylate, isopropyl acrylate, isopropyl methacrylate, n-butyl methacrylate, t-butyl acrylate, isobutyl acrylate, isobutyl methacrylate, and the like, can be cited.

As the "(meth)acrylic acid ester monomer having a cyclic skeleton in the side chain", isobornyl acrylate, cyclohexyl acrylate, cyclohexyl methacrylate, 1,4-cyclohexanedimethanol monoacrylate, tetrahydrofurfuryl methacrylate, benzyl acrylate, benzyl methacrylate, phenoxyethyl acrylate, phenoxyethyl methacrylate, 2-hydroxy-3-phenoxypropyl acrylate, 3,3,5-trimethyl cyclohexanol acrylate, cyclic trimethylolpropane formal acrylate, ethoxylated 4-cumyl phenol acrylate, dicyclopentenyloxyethyl acrylate, dicyclopentenyloxyethyl methacrylate, dicyclopentenyl acrylate, and the like, can be cited.

As the "vinyl monomer of 4 or less carbon numbers", vinyl acetate, vinyl propionate, vinyl butylate, n-propyl vinyl ether, isopropyl vinyl ether, n-butyl vinyl ether, isobutyl vinyl ether, and the like, can be cited.

As the "vinyl monomer having a cyclic skeleton in the side chain", styrene, cyclohexyl vinyl ether, norbornyl vinyl ether, norbornenyl vinyl ether, and the like, can be cited. Among them, the vinyl monomer in which the carbon number of the side chain is 4 or less, or the acrylic acid ester monomer in which the carbon number of the side chain is 4 or less, is particularly suitable.

The monomer C is preferably a (meth)acrylic acid ester monomer in which the carbon number of the side chain is 1 or less, or a (meth)acrylic acid ester monomer having a cyclic skeleton in the side chain.

Herein, as the "(meth)acrylic acid ester monomer in which the carbon number of the side chain is 1 or less", methyl methacrylate, acrylic acid, methacrylic acid, and the like, can be cited.

As the "(meth)acrylic acid ester monomer having a cyclic skeleton in the side chain", isobornyl methacrylate, 3,3,5-trimethyl cyclohexanol methacrylate, dicyclopentanyl acrylate, dicyclopentanyl methacrylate, dicyclopentenyl methacrylate, and the like, can be cited.

When the base polymer (A2) contains the (meth)acrylic acid ester copolymer or a vinyl copolymer which is formed by copolymerization of the monomer A, the monomer B, and the monomer C in a mole ratio of A:B:C=10 to 40:90 to 35:0 to 25, a peak of Tan δ can be adjusted to 0 to 20° C., a sheet shape can be maintained at normal temperature, that is, at room temperature, and adhesiveness with a peelable degree (referred to as an "tackiness") can be exerted. Also, when the base polymer (A2) is heated at a hot-meltable temperature, fluidity thereof can be exerted so that the base polymer (A2) can be filled to every corner by following a step of the bonding surface.

Thus, from such viewpoints, the mole ratio of the monomer A, the monomer B, and the monomer C in the (meth)acrylic acid ester copolymer or the vinyl copolymer which constitutes the base polymer (A2) is preferably A:B:C=10 to 40:90 to 35:0 to 25, more preferably 13 to 40:87 to 35:0 to 23, and even more preferably 15 to 40:85 to 38:2 to 20.

Further, from the same viewpoints as above, the mole ratio of the monomer A, the monomer B, and the monomer C in the (meth)acrylic acid ester copolymer or the vinyl copolymer which constitutes the base polymer (A2) is preferably B>A>C.

<Crosslinking Agent (Y)>

By crosslinking the crosslinking agent (Y) in the present adhesive sheet, the present adhesive sheet can exert high cohesive force under high temperature environment, and can obtain excellent antifoaming reliability.

As such crosslinking agent (Y), for instance, a crosslinking agent comprising an epoxy crosslinking agent, an isocyanate crosslinking agent, an oxetane compound, a silane compound, an acrylic compound, or the like, can be appropriately selected. Among them, from the viewpoint of reactivity and the strength of the obtained cured product, a polyfunctional (meth)acrylate having two or more (meth)acryloyl groups is preferable. In particular, a polyfunctional (meth)acrylate having three or more (meth)acryloyl groups is more preferable.

As such polyfunctional (meth)acrylate, for instance, in addition to ultraviolet-curable polyfunctional monomers such as 1,4-butanediol di(meth)acrylate, glycerin di(meth)acrylate, 1,6-hexanediol di(meth)acrylate, 1,9-nonanediol di(meth)acrylate, tricyclodecanedimethanol di(meth)acrylate, bisphenol A polyethoxy di(meth)acrylate, bisphenol A polypropoxy di(meth)acrylate, bisphenol F polyethoxy di(meth)acrylate, ethylene glycol di(meth)acrylate, trimethylolpropane trioxyethyl (meth) acrylate, ε-caprolactonemodified tris(2-hydroxyethyl)isocyanurate tri(meth)acrylate, pentaerythritol tri(meth)acrylate, propoxylated pentaerythritol tri(meth)acrylate, ethoxylated pentaerythritol tri(meth)acrylate, pentaerythritol tetra(meth)acrylate, propoxylated pentaerythritol tetra(meth)acrylate, ethoxylated pentaerythritol tetra(meth)acrylate, dipentaerythritol hexa(meth)acrylate, polyethylene glycol di(meth)acrylate, tris(acryloxyethyl)isocyanurate, pentaerythritol tetra(meth) acrylate, dipentaerythritol hexa(meth)acrylate, dipentaerythritol penta(meth)acrylate, tripentaerythritol hexa(meth)acrylate, tripentaerythritol penta(meth)acrylate, hydroxy pivalic acid neopentyl glycol di(meth)acrylate, di(meth)acrylate of ε-caprolactone adduct of hydroxy pivalic acid neopentyl glycol, trimethylolpropane tri(meth)acrylate, trimethylolpropanepolyethoxy tri(meth)acrylate, and ditrimethylolpropane tetra(meth)acrylate; polyfunctional acrylic oligomers such as polyester (meth)acrylate, epoxy (meth)acrylate, urethane (meth)acrylate and polyether (meth)acrylate; can be cited.

Among the above, from the viewpoints of improving tightness of contact with respect to the adherend, heat resistance, and the effect of suppressing hygrothermal whitening, a polyfunctional monomer or an oligomer containing a polar functional group is preferable. Among them, it is more preferable to use a polyfunctional (meth)acrylic acid ester having an isocyanuric ring skeleton.

The content of the crosslinking agent (Y) is not limited in particular. As a guide, the content is preferably at a proportion of 0.5 to 20 parts by mass, more preferably 1 part by mass or more or 15 parts by mass or less, and even more preferably 2 parts by mass or more or 10 parts by mass or less, with respect to 100 parts by mass of the base polymer (A2).

By containing the crosslinking agent (Y) at the above range, both the shape stability of the present adhesive sheet in an uncrosslinked state and the antifoaming reliability of the adhesive sheet in a crosslinked state can be obtained. However, the ratio may be out of such ranges depending on the balance with other element.

<Photopolymerization Initiator (Z)>

A photopolymerization initiator (Z) fulfills a function as a reaction initiating aid in a crosslinking reaction of the crosslinking agent (Y). An organic peroxidecan that generates a radical by irradiation with an active energy ray as a trigger, a photopolymerization initiator, or the like, can be suitably used. Among them, the photopolymerization initiator, in particular, a photopolymerization initiator which responds to UV light with a wavelength of 380 nm or less is preferable in terms of the controllability of the crosslinking reaction.

Meanwhile, a photopolymerization initiator which responds to light with a long wavelength of more than 380 nm is preferable in terms of being photo-curable even when the optical device constituent laminate is unlikely to transmit UV light, and allowing the responded light to reach the deep part of the present adhesive sheet sufficiently.

The photopolymerization initiator is roughly classified into two types by the radical generation mechanism: a cleavage type photopolymerization initiator that can generate a radical by cleavage and decomposition of a single bond of the photopolymerization initiator per se; and a hydrogen abstraction type photopolymerization initiator in which a photoexcited initiator and a hydrogen donor in the system can form an excited complex to allow hydrogen of the hydrogen donor to be transferred.

Of these, the cleavage type photopolymerization initiator is decomposed and converted into another compound in radical generation by light irradiation, and, if once excited, it does not have a function as a reaction initiator. For this reason, the cleavage type photopolymerization initiator is preferable since it does not remain as an active species in the adhesive sheet after the completion of the crosslinking reaction and it is not concerned that unexpected light deterioration of the adhesive sheet is brought about.

Meanwhile, the hydrogen abstraction type photopolymerization initiator is useful since it does not generate a decomposed product as the cleavage type photopolymerization initiator at the time of the radical generation reaction by irradiation with an active energy ray such as UV light, and thus it is hardly converted into a volatile component after the completion of the reaction, and damage of the adherend can be decreased.

As the cleavage type photopolymerization initiator, for instance, benzoin butyl ether, benzyl dimethyl ketal, 2-hydroxyacetophenone, bis(2,4,6-trimethylbenzoyl)-phenyl phosphine oxide, diphenyl-2,4,6-trimethylbenzoyl phosphine oxide, or any derivative thereof, can be cited.

As the hydrogen abstraction type photopolymerization initiator, for instance, benzophenone, Michler ketone, 2-ethyl anthraquinone, thioxanthone, or any derivative thereof, can be cited.

However, the photopolymerization initiator is not limited to the substances mentioned above. Any one kind of the cleavage type photopolymerization initiator and the hydrogen abstraction type photopolymerization initiator may be used, or two or more kinds of them may be used by mixing, or both of them may be used in combination for the adhesive composition B.

The content of the photopolymerization initiator (Z) is not limited in particular. As a guide, the content is preferably at a proportion of 0.1 to 10 parts by mass, more preferably 0.5 part by mass or more or 5 parts by mass or less, and even more preferably 1 part by mass or more or 3 parts by mass or less, with respect to 100 parts by mass of the base polymer (A2). By having the content of the photopolymerization initiator (Z) in the range described above, appropriate reaction sensitivity with respect to the active energy ray can be obtained.

<Other Components (W)>

The adhesive composition B may contain known components which are blended into an ordinary adhesive composition, as a component other than the above ones. For example, various kinds of additives such as a tackifying resin, an antioxidant, a light stabilizer, a metal deactivator, an antiaging agent, and a moisture absorbent can be appropriately contained, if necessary.

In addition, a reaction catalyst (tertiary amine type compound, quaternary ammonium type compound, tin laurate compound, or the like) may also be appropriately contained, if necessary.

Explanation of Terms

Generally the "sheet" refers to a thin flat product having a relatively small thickness compared to the length and width according to the definition by JIS, and generally the "film" refers to a thin flat product which has an extremely small thickness compared to the length and width and of which the maximum thickness is arbitrarily limited, and is typically provided in the form of a roll (Japanese Industrial Standards JISK6900). The boundary between the sheet and the film, however, is uncertain, and it is not necessary to literally distinguish both the sheet and the film in the present invention. Therefore, in the present invention, even when the "film" is mentioned, the "sheet" is encompassed, and even when the "sheet" is mentioned, the "film" is encompassed.

In addition, when the "panel" such as an image display panel or a protection panel is expressed, a plate, a sheet and a film are encompassed.

Herein, when the description "X to Y" (X and Y are arbitrary numbers) is made, not only the meaning "X or more and Y or less", but also the meaning "preferably more than X" or "preferably less than Y" is encompassed, unless particularly noted.

In addition, when the description "X or more" (X is an arbitrary number) is made, the meaning "preferably more than X" is also encompassed unless particularly noted, and the description "Y or less" (Y is an arbitrary number) is made, the meaning "preferably less than Y" is also encompassed unless particularly noted.

EXAMPLES

Hereinafter, the present invention will be described in more detail by way of Examples. However, the present invention is not intended to be limited thereto.

[Sample 1]

An adhesive composition 1 was produced by uniformly mixing 100 g of glycerin dimethacrylate (G101P, manufactured by Kyoeisha Chemical Co., LTD.) (B-1) as the crosslinking agent (B) and 15 g of a mixture (ESACURE TZT, manufactured by Lamberti S.p.A.) (C-1) of 2,4,6-trimethylbenzophenone and 4-methylbenzophenone as the photopolymerization initiator (C), with respect to 1 kg of an acrylic acid ester copolymer (A-1) (weight average molecular weight: 230,000) which is formed by random copolymerization of 15 parts by weight of polymethyl methacrylate macromonomer that has 2,400 of number average molecular weight, 81 parts by weight of butyl acrylate, and 4 parts by weight of acrylic acid as the main component (A).

The adhesive composition 1 was sandwiched with two release-treated polyethylene terephthalate films (referred to as a "release film", DIAFOIL MRV-V06, manufactured by Mitsubishi Plastics, Inc., thickness of 100 μm/DIAFOIL MRQ, manufactured by Mitsubishi Plastics, Inc., thickness of 75 μm), and was shaped into a sheet using a laminator so as to have a thickness of 150 μm, thereby producing an adhesive sheet 1.

A 17 mm-wide at the long side, 21 mm-wide at the short side, 40 μm-thick white print (total light transmittance: 0%) was applied at the periphery of a 180 mm×238 mm×thickness of 1 mm soda lime glass to produce a glass substrate for evaluation having an 40 μm printed step at the periphery. This glass substrate for evaluation is a substitute for an image display device constitutive member having a stepped portion and a flat surface portion on the bonding surface.

As an adherend for evaluation to be bonded onto this glass substrate for evaluation, a polarizer ("HLC2-5618", manufactured by Sanritz Co., LTD.) was pre-bonded over the entire surface on one of the sides atop a glass plate (150 mm×200 mm×t0.5 mm) to produce the adherend for evaluation.

An adhesive surface exposed by peeling off one side of the release film of the adhesive sheet 1 was bonded to the surface having the printed step of the glass substrate for evaluation with a hand roller so as to cover the printed step portion. Next, the remaining release film was peeled off, and the surface of the polarizer of the adherend for evaluation was press-bonded to the exposed adhesive surface under reduced pressure (absolute pressure: 5 kPa), then an autoclave treatment (for 20 minutes at 60° C. and 0.2 MPa) was performed for finish-adhesion to produce a laminate for evaluation 1.

Incidentally, the acrylic acid ester copolymer (A-1) is a graft copolymer having a main chain which is formed by random copolymerization of butyl acrylate, acrylic acid, and a methacryloyl group that is a polymerizable functional group of the terminal of a macromonomer as a soft segment, and a side chain component comprising a poly methyl methacrylate macromonomer as a hard segment.

A glass transition temperature (a glass transition temperature determined by a theoretical value of a polymer obtained by polymerizing the copolymer component) of the copolymer component which constitutes the stem component of the acrylic acid ester copolymer (A-1) was −50° C.

A number average molecular weight of the poly methyl methacrylate macromonomer which constitutes stem component of the acrylic acid ester copolymer (A-1) was 2,400, and a glass transition temperature of the macromonomer was 60° C., and the macromonomer was contained in the acrylic acid ester copolymer (A-1) at a proportion of 15% by mass.

[Sample 2]

An adhesive composition 2 was produced by uniformly mixing 75 g of (2,4,6-trioxo-1,3,5-triazine-1,3,5-triyl) triethylene triacrylate (B-2) (ARONIX M315, manufactured by Toagosei Co., LTD.) as the crosslinking agent and 15 g of ESACURE KTO46 (C-2) (manufactured by Lamberti S.p.A.) as the photopolymerization initiator, with respect to 1 kg of a vinyl copolymer (A-2) (weight average molecular weight: 170,000) which is formed by random copolymerization of 55 parts by mass of 2-ethylhexyl acrylate, 40 parts by mass of vinyl acetate, and 5 parts by mass of acrylic acid as the main component (A). Then, a laminate for evaluation 2 was produced in the same manner as Example 1 except that this adhesive composition 2 was used.

[Sample 3]

A laminate for evaluation was produced according to the producing example of Sample 1, and was irradiated from a side of the glass substrate for evaluation of the laminate by UV light to crosslink an adhesive sheet such that the integrated amount of light at 365 nm wavelength reached 2,000 mJ/cm$^2$, thereby serving as a laminate for evaluation 3.

Meanwhile, for an adhesive sheet which corresponds to Sample 3, the adhesive sheet 1 produced in Sample 1 was irradiated by UV light to crosslink an adhesive sheet such that the integrated amount of light at 365 nm wavelength reached 2,000 mJ/cm$^2$, thereby serving as an adhesive sheet 3.

[Sample 4]

An adhesive sheet 4 was produced according to Example 3 of Japanese Patent No. 4971529.

In other words, 50 g of nonanediol diacrylate (BISCOAT 260, manufactured by Osaka Organic Chemical Industry LTD.) (B-4) as the crosslinking agent (B) and 10 g of 4-methylbenzophenone (C-3) as the photopolymerization initiator (C) was mixed and added into 1 kg of an acrylic acid ester copolymer (A-4) which is formed by random copolymerization of 75 parts by mass of 2-ethylhexyl acrylate, 20 parts by mass of vinyl acetate, and 5 parts by mass of acrylic acid, thereby preparing an adhesive composition 4.

The adhesive composition 4 was sandwiched with two release-treated polyethylene terephthalate films (DIAFOIL MRV-V06, manufactured by Mitsubishi Plastics, Inc., thickness of 100 μm/DIAFOIL MRQ, manufactured by Mitsubishi Plastics, Inc., thickness of 75 μm), and was shaped into a sheet using a laminator so as to have a thickness of 150 μm.

Subsequently, an adhesive layer of the adhesive composition 4 was irradiated by UV light to crosslink a part of the crosslinking agent such that the UV light at 365 nm wavelength reached 1,000 mJ/cm², thereby producing an adhesive sheet 4 (thickness of 150 μm).

Then, a laminate for evaluation 4 was produced by using this adhesive sheet 4 in the same manner as Example 1.

[Sample 5]

The adhesive composition 4 prepared in Example 4 was shaped into a sheet using a laminator via two release-treated polyethylene terephthalate films (DIAFOIL MRV-V06, manufactured by Mitsubishi Plastics, Inc., thickness of 100 μm/DIAFOIL MRQ, manufactured by Mitsubishi Plastics, Inc., thickness of 75 μm) so as to have a thickness of 150 μm, thereby serving as an adhesive sheet 5. The adhesive sheet 5 was not irradiated by light, but a laminate for evaluation was produced as it is according to the producing example of Sample 4, thereby serving as a laminate for evaluation 5.

[Evaluation of Samples]

(Holding Force)

Holding force of the produced adhesive sheets 1 to 5 was measured according to JIS-Z-0237. Specifically, each of the adhesive sheets 1 to 5 produced in Examples and Comparative Examples was cut to have a size of 40 mm×50 mm, the mold release film on one of the sides was peeled off, a backing PET film (DIAFOIL S-100, manufactured by Mitsubishi Plastics, Inc., thickness of 38 μm) was adhered thereon with a hand roller. Then, this was cut into a strip shape of 25 mm-width×100 mm-length to serve as a test strip.

Next, the remaining mold release film was peeled off, and adhered with a hand roller against a SUS plate (120 mm×50 mm×thickness of 1.2 mm) so as to have an adhesion surface area of 20 mm×20 mm.

Thereafter, the test strip was cured under an atmosphere of 40° C. for 15 minutes, then, a weight of 500 gf (4.9 N) was applied to the test strip in the vertical direction and left alone for 30 minutes, and after that, a length (mm) by which the adhesion position between the SUS and the test strip shifted downward, that is, a shifted amount, was measured. Meanwhile, for the sheet that the weight thereon was fallen down, a time (minutes) until the weight fell down was measured. In so doing, when the shifted length of the test strip at 40° C. was 5 mm or less, it is suggested that the sheet has sufficient holding force, and processability and storage stability thereof are excellent.

Incidentally, "<0.5 mm" in the table means a state that the shifted length is less than 0.5 mm, and there is almost no shift.

Similarly, the above test was performed under an atmosphere of 80° C., then a shifted length of the adhesion position after being left alone for 30 minutes, or a time until the weight fell down was measured. In so doing, when the shifted length at 80° C. was 10 mm or more, or the weight fell down within 30 minutes, it can be said that the sheet has excellent repeelability due to heating.

(Transparency)

An adhesive surface exposed by peeling off one side of the mold release film of the adhesive materials 1 to 5 was applied to a soda lime glass (82 mm×53 mm×thickness of 0.5 mm) by roll compression. Next, the remaining mold release film was peeled off, and a soda lime glass (82 mm×53 mm×thickness of 0.5 mm) was bonded thereon, and then, an autoclave treatment (for 20 minutes at 80° C. and a gauge pressure of 0.2 MPa) was performed for finish-adhesion to produce a laminate.

For the laminate, the total light transmittance (according to JIS K7361-1) and the haze value (according to JIS K7136) were measured using a haze meter (NDH5000, manufactured by Nippon Denshoku Industries Co., LTD.), respectively.

(Bonding Force)

One side of the mold release film of the adhesive sheets 1, 2, 4, and 5 was peeled off, and then a PET film (DIAFOIL T 100, manufactured by Mitsubishi Plastics, Inc., thickness of 50 μm) having a thickness of 50 μm as a backing film was bonded thereon.

The above laminate article was cut into a size of 150 mm-length×10 mm-width, and then the adhesive surface exposed by peeling off the remaining mold release film was applied to a soda lime glass by roll compression. The bonded article was subjected to an autoclaving treatment (for 20 minutes at 80° C. and a gauge pressure of 0.2 MPa) for finish-adhesion to serve as an uncured sample for peel force measurement.

In addition, the sample produced in the same procedure as the above was irradiated from the backing film side with UV light to cure the adhesive sheet such that the integrated amount of light at 365 nm reached 2,000 mJ/cm², and then this was aged for 15 hours at 23° C. and 50% RH to serve as a cured sample for peel force measurement.

(Processing Suitability)

Each of the adhesive sheets 1 to 5 with which the mold release file is laminated was cut to 100 sheets using a Thomson punching machine with a Thomson blade of 50 mm×80 mm, and the shape of the edges thereof was observed. Those in which a crushing of the edges, a protrusion of the adhesive, or a lifting of the mold release film was observed in 20 sheets or more were evaluated as "X", and those in which there were no such phenomenons in 20 sheets or more were judged as "◯".

TABLE 1

|  |  | Sample 1 | Sample 2 | Sample 3 | Sample 4 | Sample 5 |
|---|---|---|---|---|---|---|
| Main component (A) | A-1 | 100 |  | 100 |  |  |
|  | A-2 |  | 100 |  |  |  |
|  | A-4 |  |  |  | 100 | 100 |
| Crosslinking agent (B) | B-1 | 10 |  | 10 |  |  |
|  | B-2 |  | 7.5 |  |  |  |
|  | B-4 |  |  |  | 5 | 5 |
| Photopolymerization initiator (C) | C-1 | 1.5 |  | 1.5 |  |  |
|  | C-2 |  | 1.5 |  |  |  |
|  | C-3 |  |  |  | 1 | 1 |

TABLE 1-continued

|  |  | Sample 1 | Sample 2 | Sample 3 | Sample 4 | Sample 5 |
|---|---|---|---|---|---|---|
| Holding force | (1) 40° C. (Target: less than 5 mm) | 3 mm | 2 mm | (<1 mm) | 2 mm | 5 min. fall down |
|  | (2) 80° C. (Target: 10 mm or more) | 5 min. fall down | 11 min. fall down | (<1 mm) | 4 mm | 10 sec. fall down |
| Uncured adhesive force (N/cm) | (3) 23° C. (Target: 5 N/cm or more) | 8 | 20 | — | 13 | 18 |
|  | (4) 85° C. (Target: less than 2 N/cm) | 0.2 | 0.5 | — | 1 | 0.2 |
| Cured adhesive force (N/cm) | (5) 23° C. (Target: 5 N/cm or more) | 8 | 18 | — | 9 | 10 |
|  | (6) 85° C. (Target: 3 N/cm or more) | 5 | 7 | — | 1 | 1 |
| Total light transmittance |  | 92% | 92% | 92% | 92% | 92% |
| Haze |  | 0.3% | 0.3% | 0.3% | 0.3% | 0.3% |
| Processing suitability |  | ○ | ○ | ○ | ○ | X |
| Repeelability |  | ○ | ○ | X | X | ○ |

(Considerations)

The adhesive sheets of Samples 1, 2 and 5 were excellent in reworkability, since the shifted amount of holding force thereof at 80° C. was large and heating fluidity thereof was high, thereby all of the bonded members were rapidly separated within 15 minutes in the repeelability evaluation described below. In addition, it was resulted that the adhesive sheets of Samples 1 to 4 had excellent processing suitability as well, as the shape thereof before heating was maintained firmly since the holding force at 40° C. was high. Further, for the adhesive sheets of Samples 1 and 2, the members could be bonded firmly by irradiating the bonded article with light, since the sheets had photo-curability.

In contrast, for the adhesive sheets of Samples 3 and 4, the bonded members could not be separated, as it was not able to obtain sufficient heating fluidity even when heated since the adhesive sheets were the primary crosslinked adhesive materials by UV light.

The adhesive sheet of Sample 5 was used as the state that the UV crosslinking was not performed on the adhesive composition of Sample 4. Although it exhibited high heating fluidity and ease of repeeling, holding force at 40° C. was low, and an inferior cutting due to stickiness and overflow of the adhesive was observed since the adhesive sheet was flowed even at room temperature, thereby exhibiting inferior processing suitability.

<Evaluation for Recycling Optical Device Constituent Members/Reworkability of Optical Device Constituent Laminate>

For the produced laminates for evaluation 1 to 5, the samples were stored and preheated at temperature of 80° C. for 15 minutes.

As illustrated in FIG. 2, a nylon wire (0.21 mmφ) as the linear member was hung in between the members of the preheated laminate from one long side, and each weight of 1 kg was suspended vertically at the both ends of the wire respectively. A load of total 2 kg was thus applied to the adhesive sheet of the laminate for evaluation, and it was confirmed whether the wire passed through the adhesive sheet and the bonded member thereof was divided.

In so doing, a weight of the load applied by the liner member 5 and an elapsed time since the load was applied by the liner member 5 until the bonded member was divided were measured, and the laminates were evaluated on the basis of these values as follows.

Specifically, those in which the adhesive sheet was divided and the member thereof was separated within 15 minutes were judged as "O", and those in which the wire passed through in 15 minutes or more, or the wire was not able to pass through, thereby not separating the member were judged as "X".

In the optical device constituent members 2(3) to which the one-side transparent adhesive material 1A as divided above adhered, as illustrated in FIG. 10 (A) to (C), the adhesive material 12 was superposed and bonded on the one-side transparent adhesive material 1A of the optical device constituent members 2(3) to which the one-side transparent adhesive material 1A adhered, then the one-side transparent adhesive material 1A was peeled off together with the adhesive material 12 by pulling the adhesive material 12 to the parallel direction with the planar direction, that is, to the shear direction of the adhesion interface between the one-side transparent adhesive material and the optical device constituent members.

The invention claimed is:

1. A method for recycling optical device constituent members,
   comprising:
   heating at least an transparent adhesive material of an optical device constituent laminate having a constitution in which two optical device constituent members are bonded via the transparent adhesive material;
   hanging a linear member along an end edge of the transparent adhesive material of the optical device constituent laminate;
   dividing the transparent adhesive material by applying a load by the linear member;
   and producing the two optical device constituent members to which a divided one-side transparent adhesive material adheres.

2. The method for recycling optical device constituent members according to claim 1, wherein the transparent adhesive material is heated to a temperature of 60 to 100° C.

3. The method for recycling optical device constituent members according to claim 1, comprising following steps: standing the optical device constituent laminate; hanging the linear member along the end edge of the transparent adhesive material located at an upper end edge of the optical device constituent laminate; and suspending a weight at an end of the linear member, thereby applying the load by the linear member.

4. The method for recycling optical device constituent members according to claim 1, wherein an adhesive material is superposed and bonded on the transparent adhesive material of the optical device constituent members to which a divided one-side transparent adhesive material adheres, and the transparent adhesive material is peeled off from the optical device constituent members by pulling the adhesive material to the parallel direction with the planar direction, that is, to the shear direction of the adhesion interface between the one-side transparent adhesive material and the optical device constituent members.

5. The method for recycling optical device constituent members according to claim 1, wherein the transparent adhesive material meets the following conditions (1) and (2):
   (1) for a sheet with the thickness of 150 μm comprising the pre-crosslinked transparent adhesive material, a shifted length at a temperature of 40° C. with respect to a SUS plate is less than 5 mm in holding force measurement according to JIS-Z-0237; and
   (2) for a sheet with the thickness of 150 μm comprising the pre-crosslinked transparent adhesive material, a shifted length at a temperature of 80° C. with respect to a SUS plate is 10 mm or more in holding force measurement according to JIS-Z-0237.

6. The method for recycling optical device constituent members according to claim 1, wherein the transparent adhesive material meets the following conditions (3) and (4):
   (3) a 180° peel force is 5 N/cm or more when the adhesive sheet with the thickness of 150 μm comprising the pre-crosslinked transparent adhesive material is superposed on a soda lime glass, and the adhesive sheet and the soda lime glass are roll-crimped by reciprocating a roller of 2 kg one time, and then the adhesive sheet is peeled off from the soda lime glass at a temperature of 23° C., a peel angle of 180°, and a peel rate of 60 mm/min; and
   (4) a 180° peel force is less than 2 N/cm when the adhesive sheet with the thickness of 150 μm comprising the pre-crosslinked transparent adhesive material is superposed on a soda lime glass, and the adhesive sheet and the soda lime glass are roll-crimped by reciprocating a roller of 2 kg one time, and then the adhesive sheet is peeled off from the soda lime glass at a temperature of 85° C., a peel angle of 180°, and a peel rate of 60 mm/min.

7. The method for recycling optical device constituent members according to claim 1, wherein the transparent adhesive material meets the following conditions (5) and (6):
   (5) a 180° peel force is 5 N/cm or more when the adhesive sheet with the thickness of 150 μm comprising the pre-crosslinked transparent adhesive material is superposed on a soda lime glass, and the adhesive sheet and the soda lime glass are roll-crimped by reciprocating a roller of 2 kg one time, and then the adhesive sheet is peeled off from the soda lime glass at a temperature of 23° C., a peel angle of 180°, and a peel rate of 60 mm/min in a state of that the transparent adhesive material is crosslinked by irradiating light to the transparent adhesive material such that the light at 365 nm wavelength reaches 2,000 mJ/cm; and
   (6) a 180° peel force is 3 N/cm or more when the adhesive sheet with the thickness of 150 μm comprising the pre-crosslinked transparent adhesive material is superposed on a soda lime glass, and the adhesive sheet and the soda lime glass are roll-crimped by reciprocating a roller of 2 kg one time, and then the adhesive sheet is peeled off from the soda lime glass at a temperature of 85° C., a peel angle of 180°, and a peel rate of 60 mm/min in a state of that the transparent adhesive material is crosslinked by irradiating light to the transparent adhesive material such that the light at 365 nm wavelength reaches 2,000 mJ/cm$^2$.

8. The method for recycling optical device constituent members according to claim 1, wherein the transparent adhesive material is a transparent adhesive material formed from an adhesive composition containing an acrylic series copolymer (A1) which comprises a graft copolymer having a macromonomer as branch component, a crosslinking agent (B), and a photopolymerization initiator (C).

9. The method for recycling optical device constituent members according to claim 1, wherein the transparent adhesive material is formed from an adhesive composition containing a base polymer (A2) which comprises a (meth) acrylic acid ester copolymer or a vinyl copolymer having a weight average molecular weight of 50,000 to 400,000, a crosslinking agent (B), and a photopolymerization initiator (C), wherein said adhesive composition containing a base polymer (A2) is formed by copolymerization of a monomer a1, a monomer a2, and a monomer a3 in a mole ratio of a1:a2:a3=10 to 40:90 to 35:0 to 25;
   wherein
      in the monomer a1, a glass transition temperature of a homopolymer is less than 0° C. when the homopolymer of the monomer a1 is produced,
      in the monomer a2, a glass transition temperature of a homopolymer is 0° C. or more and less than 80° C. when the homopolymer of the monomer a2 is produced, and
      in the monomer a3, a glass transition temperature of a homopolymer is 80° C. or more when the homopolymer of the monomer a3 is produced.

10. The method for recycling optical device constituent members according to claim 1, wherein the optical device constituent members comprises any, or a combination of two or more species from a group consisting of a touch panel, an image display panel, a surface protection panel, and a polarization film.

11. A reworkability evaluation method of the optical device constituent laminate, wherein
   an optical device constituent laminate having a constitution in which two optical device constituent members are bonded is used as an evaluation target,
   and comprising:
   heating at least a transparent adhesive material that bonds the two optical device constituent members;
   hanging a linear member along an end edge of the transparent adhesive material of the optical device constituent laminate;
   dividing the transparent adhesive material into two members by applying a load by the linear member;
   and thereby measuring a weight of the load applied by the liner member and an elapsed time until being divided.

* * * * *